United States Patent
Thomas et al.

(12) 
(10) Patent No.: US 6,225,527 B1
(45) Date of Patent: May 1, 2001

(54) PLANT PATHOGEN RESISTANCE GENES AND USES THEREOF

(75) Inventors: Colwyn Martin Thomas, Norwich (GB); Peter John Balint-Kurti, Bethesda, MD (US); David Allen Jones, Canberra (AU); Jonathan Dallas George Jones, Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 08/945,983

(22) PCT Filed: May 13, 1996

(86) PCT No.: PCT/GB96/01155

§ 371 Date: Nov. 12, 1997

§ 102(e) Date: Nov. 12, 1997

(87) PCT Pub. No.: WO96/35790

PCT Pub. Date: Nov. 14, 1996

(30) Foreign Application Priority Data

Nov. 5, 1995 (GB) .................................. 9509575

(51) Int. Cl.⁷ .............................. A01H 1/00; A01H 9/00; A01H 5/00; C12N 15/82
(52) U.S. Cl. ........................ 800/279; 435/69.1; 435/468; 435/410; 435/411; 435/419; 435/220.1; 536/23.74; 536/23.1; 800/278; 800/288; 800/290; 800/295; 800/317.4
(58) Field of Search ............................ 536/23.6, 23.74, 536/23.1; 800/205, DIG. 73, 278, 279, 288, 290, 295, 317.4; 435/69.1, 468, 410, 411, 419

(56) References Cited

FOREIGN PATENT DOCUMENTS

| | | |
|---|---|---|
| WO 95 05731 | 3/1995 | (WO) . |
| WO 95 18230 | 7/1995 | (WO) . |
| WO 95 31564 | 11/1995 | (WO) . |

OTHER PUBLICATIONS

Napoli et al. The Plant Cell. 1989. vol. 2: 278–289.*
Agrios. Plant Pathogen. 1978. Academic Press.*
Trends in Genetics, vol. 11, Feb. 1995, pp. 63–68, XP002006911 Tanksley, S.D., et al.: "Chormosome landing: a paradigm for map–based gene cloning in plants with large genomes." See the whole document.

Theoretical and Applied Genetics 88 (6–7). 1994. 691–700., XO000574061 Balint–Kurti P J et al: "RFLP linkage analysis of the Cf–4 and Cf–9 genes for resistance to *Cladosporium fulvum* in tomato." See the whole document.

Plant Physiology, vol. 101, 1993, pp. 709–712, XP002006913 Cornelissen, B.J.C., et al.: "Strategies for control of fungal diseases with transgenic plants" see p. 709, left–hand column, last paragraph—p. 710, left–hand column, paragraph 1.

Cell, vol. 80, Feb. 10, 1995, pp. 363–366. XP002006912 Dangl, J.L.: Pièce de Résistance: novel classes of plant diseasse resistance genes: see p. 365, right–hand column, line 13–line 24.

Science, vol. 266, Nov. 4, 1994, pp. 789–793, XP002007124 Jones, D.A., et al.: "Isolation of the tomato Cf–9 gene for resistance to *Cladosporium fulvum* by transposon tagging" see the whole document.

Journal of Cellular Biochemistry Supplement. Keystone Symposium Held Mar. 29–Apr. 4, 1995, vol. 21a, 1995, p. 485 XP002007014 Dixon, M.S., et al.: "Cloning and characterisation of the Cf–2 disease resistance gene related family members and the corresponding nnull locus" see abstract J6–203.

Science, vol. 268, May 5, 1995, pp. 661–667, XP002007125 Staskawicz, B.J., et al.: "Molecular genetics of plant disease resistance" see the whole document.

Chemical Abstracts, vol. 118, No. 17, Apr. 26, 1993 Columbus, Ohio US; abstract No. 161928, Jones J.D.G. et al: "Prospects for establishing a tomato gene tagging system using the maize transposon Activator (Ac)" XP002014516 see abstract 7 Proc.—R. Soc. Edinburgh, Sect. B: Biol. Sci. (19992), 99(3–4), 107–19.

* cited by examiner

*Primary Examiner*—Paula Hutzell
*Assistant Examiner*—Ousama Zaghmout
(74) *Attorney, Agent, or Firm*—Nixon & Vanderhye P.C.

(57) ABSTRACT

The tomato Cf-4 gene has been isolated by positional cloning and its sequence provided, along with the encoded amino acid sequence. DNA encoding the polypeptide, alleles, mutants and derivatives thereof, and DNA encoding amino acid sequences showing a significant degree of homology thereto may be introduced into plant cells and the encoded polypeptide expressed, conferring pathogen resistance on plants comprising such cells and descendants thereof. The Cf-4 sequence shows a high degree of homology to Cf-9 and comprises leucine rich repeats.

21 Claims, 14 Drawing Sheets

Figure 4

Figure 1:
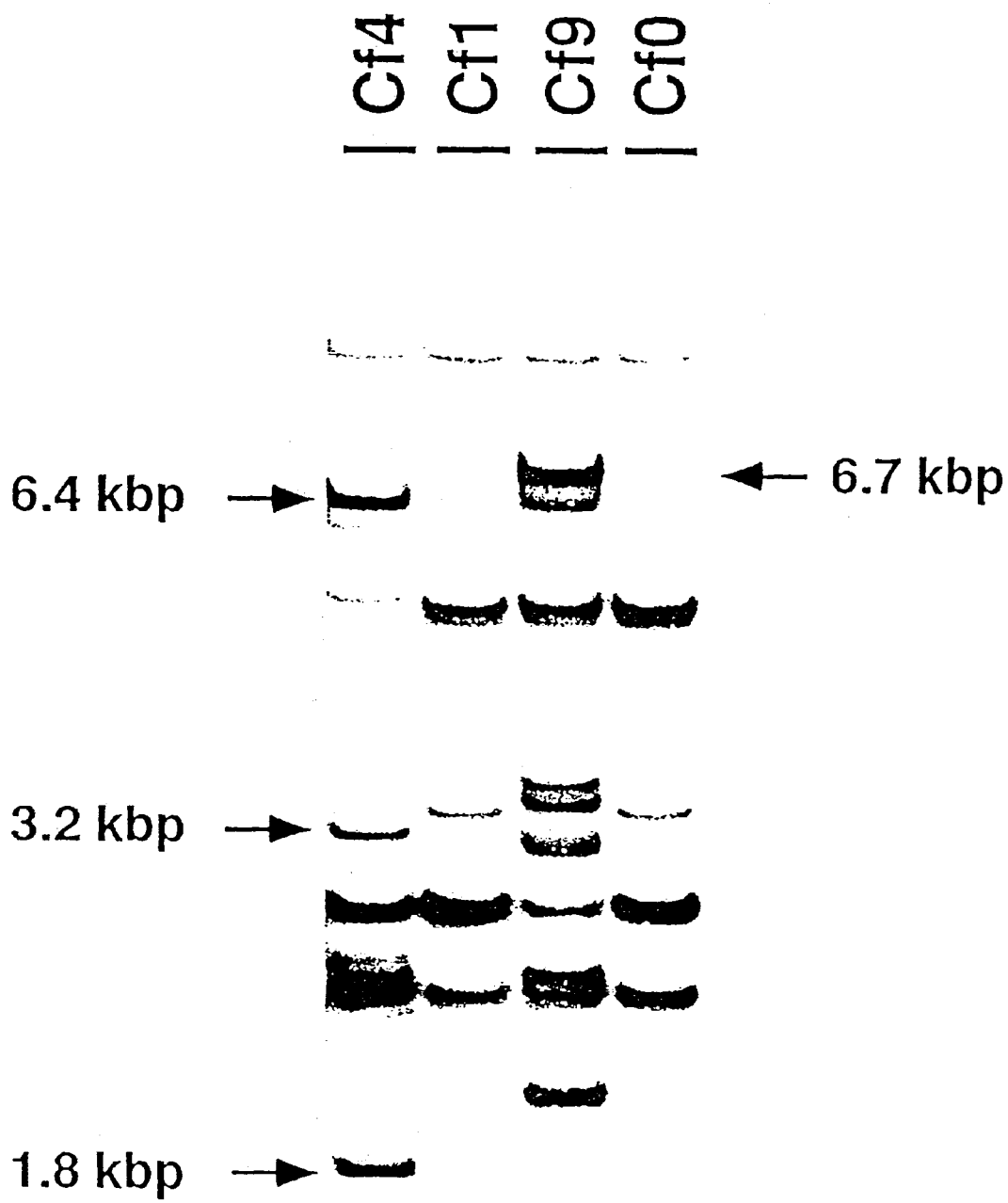

```
    ATCGATGGGATTTGTTCTCTTTTCACAATTGCCTTCATTTCTTCTTGTCTCTACACTTCT
  1 ---------+---------+---------+---------+---------+---------+  60
    TAGCTACCCTAAACAAGAGAAAAGTGTTAACGGAAGTAAAGAAGAACAGAGATGTGAAGA

M  G  F  V  L  F  S  Q  L  P  S  F  L  L  V  S  T  L  L

CTTATTCCTAGTAATATCCCACTCTTGCCGTGCCAAAGCCCCCAAAACTCAACCATACAA
 61 ---------+---------+---------+---------+---------+---------+ 120
    GAATAAGGATCATTATAGGGTGAGAACGGCACGGTTTCGGGGGTTTTGAGTTGGTATGTT

L  F  L  V  I  S  H  S  C  R  A  K  A  P  K  T  Q  P  Y  N

CCCATGCAAGCCCCAAGAAGTCATCGACACCAAGTGTATGGGTCCCAAGGATTGTCTCTA
121 ---------+---------+---------+---------+---------+---------+ 180
    GGGTACGTTCGGGGTTCTTCAGTAGCTGTGGTTCACATACCCAGGGTTCCTAACAGAGAT

P  C  K  P  Q  E  V  I  D  T  K  C  M  G  P  K  D  C  L  Y

CCCGAACCCCGACAGTTGTACAACCTACATACAGTGTGTACCGCTCGACGAAGTTGGCAA
181 ---------+---------+---------+---------+---------+---------+ 240
    GGGCTTGGGGCTGTCAACATGTTGGATGTATGTCACACATGGCGAGCTGCTTCAACCGTT

P  N  P  D  S  C  T  T  Y  I  Q  C  V  P  L  D  E  V  G  N

TGCGAAGCCTGTGGTTAAGCCATGTCCAAAAGGACTGCAGTGGAACGATAACGTTGGCAA
241 ---------+---------+---------+---------+---------+---------+ 300
    ACGCTTCGGACACCAATTCGGTACAGGTTTTCCTGACGTCACCTTGCTATTGCAACCGTT

A  K  P  V  V  K  P  C  P  K  G  L  Q  W  N  D  N  V  G  K

GAAGTGGTGCGACTATCCAAACCTGAGTACGTGTCCGGTAAAGACGCCGCAACCGAAGCC
301 ---------+---------+---------+---------+---------+---------+ 360
    CTTCACCACGCTGATAGGTTTGGACTCATGCACAGGCCATTTCTGCGGCGTTGGCTTCGG

K  W  C  D  Y  P  N  L  S  T  C  P  V  K  T  P  Q  P  K  P

GAAGAAGGGAGGTGTCGGAGGGAAGAAGGCGTCGGTTGGACATCCTGGCTATTGAGTCGG
361 ---------+---------+---------+---------+---------+---------+ 420
    CTTCTTCCCTCCACAGCCTCCCTTCTTCCGCAGCCAACCTGTAGGACCGATAACTCAGCC

K  K  G  G  V  G  G  K  K  A  S  V  G  H  P  G  Y

ACAAGAAAGGGGATGGCTGTAACAGTTCTGGTACCAGAGCTATCGTGCTAGGGGATCCGT
421 ---------+---------+---------+---------+---------+---------+ 480
    TGTTCTTTCCCCTACCGACATTGTCAAGACCATGGTCTCGATAGCACGATCCCCTAGGCA

CGAC
481 ----
    GCTG
```

FIGURE 5

```
  1  GACCAAACTG GACTCCTGCT CCGTCTTCCA TCAGCAGGTC AATTCTCGTG

51  GAAAATTAGC TCGAGGTGGC GCACTATGTG AGGTAGCTAG TACTAAATGT

101  TTATTTGCGT AATTTGTGCT ATATATACCT CATCTAAATT ATTGAATAGA

151  CACACAAAGC AAACATCTCT TAATTAGTTT TGATCATTTT TAGTGCAGAA

201  ATGGGTTGTG TAAAACTTGT GTTTTTCATG CTATATGTCT TTCTCTTTCA

251  ACTTGTTTCC TCGTCATCCT TACCTCATTT GTGCCCCGAA GATCAAGCTC

301  TTGCTCTTCT AGAATTCAAG AACATGTTTA CCGTTAATCC TAATGCTTCT

351  GATTATTGTT ACGACAGAAG AACTCTTTCT TGGAACAAAA GCACAAGTTG

401  CTGCTCATGG GATGGCGTTC ATTGTGACGA AACGACAGGA CAAGTGATTG

451  AGCTTGACCT CCGTTGCATC CAACTTCAAG GCAAGTTTCA TTCCAATAGT

501  AGCCTCTTTC AACTCTCCAA TCTCAAAAGG CTTGATTTGT CTTATAATGA

551  TTTCACTGGA TCGCCCATTT CACCTAAATT TGGTGAGTTT TCAGATTTGA

601  CGCATCTCGA TTTGTCGCAT TCAAGTTTTA GGGGTGTAAT CCCTTCTGAA

651  ATCTCTCATC TTTCTAAACT ATACGTTCTT CGTATTAGTC TAAATGAGCT

701  TACTTTTGGT CCTCACAATT TTGAATTGCT TCTTAAGAAC TTGACCCAAT

751  TAAAAGTGCT CGACCTTGAA TCTATCAACA TCTCTTCCAC TATTCCTTTG

801  AATTTCTCTT CTCATTTAAC AAATCTATGG CTTCCATACA CAGAGTTACG

851  TGGGATATTG CCCGAAAGAG TTTTCCACCT TTCCGACTTA GAATTTCTCG

901  ATTTATCAAG CAATCCCCAG CTCACGGTTA GGTTTCCCAC AACCAAATGG
```

```
 951  AATAGCAGTG CATCACTCAT GAAGTTATAT CTCTATAATG TGAATATTGA

1001  TGATAGGATA CCTGAATCAT TTAGCCATCT AACTTCACTT CATAAGTTGT

1051  ACATGAGTCG TTCTAATCTG TCAGGGCCTA TTCCTAAACC TCTATGGAAT

1101  CTCACCAACA TAGTGTTTTT GGACCTTAAT AATAACCATC TTGAAGGACC

1151  AATTCCATCC AACGTAAGCG GACTACGTAA CCTACAAATA CTTTGGTTGT

1201  CATCAAACAA CTTAAATGGG AGTATACCAT CCTGGATATT CTCCCTTCCA

1251  TCACTGATAG GGTTAGACTT GAGCAATAAC ACTTTCAGTG GAAAAATTCA

1301  AGAGTTCAAG TCCAAAACAT TAAGTACCGT TACTCTAAAA CAAAATAAGC

1351  TAAAAGGTCC TATTCCGAAT TCACTCCTAA ACCAGAAGAA CCTACAATTC

1401  CTTCTCCTTT CACACAATAA TATCAGTGGA CATATTTCTT CAGCTATCTG

1451  CAATCTGAAA ACATTGATAT TGTTAGACTT GGGAAGTAAT AATTTGGAGG

1501  GAACAATCCC GCAATGCGTG GTTGAGAGGA ACGAATACCT TTCGCATTTG

1551  GATTTGAGCA ACAACAGACT TAGTGGGACA ATCAATACAA CTTTTAGTGT

1601  TGGAAACATT TTAAGGGTCA TTAGCTTGCA CGGGAATAAG CTAACGGGGA

1651  AAGTCCCACG ATCTATGATC AATTGCAAGT ATTTGACACT ACTTGATCTA

1701  GGTAACAATA TGTTGAATGA CACATTTCCA AACTGGTTGG GATACCTATT

1751  TCAATTGAAG ATTTTAAGCT TGAGATCAAA TAAGTTGCAT GGTCCCATCA

1801  AATCTTCAGG GAATACAAAC TTGTTTATGG GTCTTCAAAT TCTTGATCTA

1851  TCATCTAATG GATTTAGTGG GAATTTACCC GAAAGAATTT TGGGGAATTT
```

```
1901  GCAAACCATG AAGGAAATTG ATGAGAGTAC AGGATTCCCA GAGTATATTT

1951  CTGATCCATA TGATATTTAT TACAATTATT TGACGACAAT TTCTACAAAG

2001  GGACAAGATT ATGATTCTGT TCGAATTTTG GATTCTAACA TGATTATCAA

2051  TCTCTCAAAG AACAGATTTG AAGGTCATAT TCCAAGCATT ATTGGAGATC

2101  TTGTTGGACT TCGTACGTTG AACTTGTCTC ACAATGTCTT GGAAGGTCAT

2151  ATACCGGCAT CATTTCAAAA TTTATCAGTA CTCGAATCAT GGATCTCTC

2201  ATCTAATAAA ATCAGCGGAG AAATTCCGCA GCAGCTTGCA TCCCTCACAT

2251  TCCTTGAAGT CTTAAATCTC TCTCACAATC ATCTTGTTGG ATGCATCCCC

2301  AAAGGAAAAC AATTTGATTC GTTCGGGAAC ACTTCGTACC AAGGGAATGA

2351  TGGGTTACGC GGATTTCCAC TCTCAAAACT TTGTGGTGGT GAAGATCAAG

2401  TGACAACTCC AGCTGAGCTA GATCAAGAAG AGGAGGAAGA AGATTCACCA

2451  ATGATCAGTT GGCAGGGGGT TCTCGTGGGT TACGGTTGTG GACTTGTTAT

2501  TGGACTGTCC GTAATATACA TAATGTGGTC AACTCAATAT CCAGCATGGT

2551  TTTCGAGGAT GGATTTAAAG TTGGAACACA TAATTACTAC GAAAATGAAA

2601  AAGCACAAGA AAAGATATTA GTGAGTAGCT ATACCTCCAG GTATTCCACT

2651  TGATCATTAT CTTTCAGAAG ATTATTTTTT GTATATCGAT GAAATTATCG

2701  ACCTCCTTCA TCCTCAAAGC TCTTAACTTT CACTCTTCAT TTTTGAAAAT

2751  TTCAGGATTC AAAGATTTCC GAGTTCCCAG TTGCTTGGGA TGCAGATAAA

2801  AGCCTTTTTA TCTTTCATAG TTTCTTATCC TATGAATAAA GATTTATTT

2851  TCATTTGTCT ATGGCACGTA GATATGTTCC GTCACTAAAA ACATTGTATT
```

```
2901  TCTCTCAACT CTTTCGTCAC ATGATATCAA AGAACACTTG ACTTCAATTA

2951  AGTTACTGTA GTCTGCTATT TTAATTTCTT CCATTGAAAC ACAACTGACG

3001  TATCTTGAGA AAGAGACTAT GATCTCAGAA ATGGGAATCT CCCAATCCAA

3051  AACTCGAAA ATCTAGTATC AAACACACCC GACCCTGCAG
```

FIGURE 6

```
  1  MGCVKLVFFM LYVFLFQLVS SSSLPHLCPE DQALALLEFK NMFTVNPNAS
 51  DYCYDRRTLS WNKSTSCCSW DGVHCDETTG QVIELDLRCI QLQGKFHSNS
101  SLFQLSNLKR LDLSYNDFTG SPISPKFGEF SDLTHLDLSH SSFRGVIPSE
151  ISHLSKLYVL RISLNELTFG PHNFELLLKN LTQLKVLDLE SINISSTIPL
201  NFSSHLTNLW LPYTELRGIL PERVFHLSDL EFLDLSSNPQ LTVRFPTTKW
251  NSSASLMKLY LYNVNIDDRI PESFSHLTSL HKLYMSRSNL SGPIPKPLWN
301  LTNIVFLDLN NNHLEGPIPS NVSGLRNLQI LWLSSNNLNG SIPSWIFSLP
351  SLIGLDLSNN TFSGKIQEFK SKTLSTVTLK QNKLKGPIPN SLLNQKNLQF
401  LLLSHNNISG HISSAICNLK TLILLDLGSN NLEGTIPQCV VERNEYLSHL
451  DLSNNRLSGT INTTFSVGNI LRVISLHGNK LTGKVPRSMI NCKYLTLLDL
501  GNNMLNDTFP NWLGYLFQLK ILSLRSNKLH GPIKSSGNTN LFMGLQILDL
551  SSNGFSGNLP ERILGNLQTM KEIDESTGFP EYISDPYDIY YNYLTTISTK
601  GQDYDSVRIL DSNMIINLSK NRFEGHIPSI IGDLVGLRTL NLSHNVLEGH
651  IPASFQNLSV LESLDLSSNK ISGEIPQQLA SLTFLEVLNL SHNHLVGCIP
701  KGKQFDSFGN TSYQGNDGLR GFPLSKLCGG EDQVTTPAEL DQEEEEEDSP
751  MISWQGVLVG YGCGLVIGLS VIYIMWSTQY PAWFSRMDLK LEHIITTKMK
801  KHKKRY
```

Cf-4

A  MGCVKLVFFMLYVFLFQLVSSSS

B  LPHLCPEDQALALLEFKNMFTVNPNASDYCYD..
........RRTLSWNKSTSCCSWDGVHCDETTGQ

C
```
      VIELDLRCIQLQGKFHSNSS
LFQLSNLKRLDLSYNDFTGSPISPK
FGEFSDLTHLDLSHSSFRGVIPSE
ISHLSKLYVLRISLNELTFGPHNFELL
LKNLTQLKVLDLESINISSTIPL
NFSSHLTNLWLPYTELRGILPER
VFHLSDLEFLDLSSNPQLTVRFPTTK
WNSSASLMKLYLYNVNIDDRIPES
FSHLTSLHKLYMSRSNLSGPIPKP
LWNLTNIVFLDLNNNHLEG....
.........................
.................PIPSN
VSGLRNLQILWLSSNNLNGSIPSW
IFSLPSLIGLDLSNNTFSGKIQEF
   KSKTLSTVTLKQNKLKGPIPNS
LLNQKNLQFLLLSHNNISGHISSA
ICNLKTLILLDLGSNNLEGTIPQCV
VERNEYLSHLDLSNNRLSGTINTT
FSVGNILRVISLHGNKLTGKVPRS
MINCKYLTLLDLGNNMLNDTFPNW
LGYLFQLKILSLRSNKLHGPIKSSGN
TNLFMGLQILDLSSNGFSGNLPERI
LGNLQTMKEIDEST GFPEYISDPY
DIYYNYLTTI  STKGQD YDSVRI
   LDSNMIINLSKNRFEGHIPSI
IGDLVGLRTLNLSHNVLEGHIPAS
FQNLSVLESLDLSSNKISGEIPQQ
LASLTFLEVLNLSHNHLVGCIPKG
```

D  KQFDSFGNTSYQGNDGLRGFPLSKLCGG

E  EDQVTTPAELDQEEEEED

F  SPMISWQGVLVGYGCGLVIGLSVIYIMWSTQYPAWFS

G  RMDLKLEHIITTKMKKHKKRY

```
40 KNMFTINPNASDYCYDIRTYVDIQSYPRTLSWNKSTSCCS 79  Cf-9
   |||||:||||||||||           ·||||||||||||
40 KNMFTVNPNASDYCYD..........RRTLSWNKSTSCCS 69  Cf-4
```

B

```
           LRR 9                     LRR 10
     ┌──────────────────────┐  ┌─────────────────────┐ ┌
285  FSHLTSLHELYMGRCNLSGPIPKP  LWNLTNIVFLHLGDNHLEGPISH FTI 334  Cf-9
     ||||||||·|||:|:||||||||   ||||||||||·|·:|||||
274  FSHLTSLHKLYMSRSNLSGPIPKP  LWNLTNIVFLDLNNNHLEG     ....... 315 Cf-4
     └──────────────────────┘  └─────────────────────┘
           LRR 9                     LRR 10
```

```
          LRR 11                    LRR 12
     ┌──────────────────────┐ ┌──────────────────────┐
335  FEKLKRLSLVNNNFDGGLEF     LSFNTQLERLDLSSNSLTGPIPSN  ISGLQN 384 Cf-9
                                                       |||||:|||·|
316  ....................... ......................PIPSN VSGLRN 327 Cf-4
                                                     └────┘└────
```

```
           LRR 13                    LRR 14
     ┌──────────────────────┐ ┌──────────────────────┐
385  LECLYLSSNHLNGSIPSW      IFSLPSLVELDLSNNTFSGKIQEF 426       Cf-9
     |:·|:||||:|||||||||     |||||||::||||||||||||||||
328  LQILWLSSNNLNGSIPSW      IFSLPSLIGLDLSNNTFSGKIQEF 369       Cf-4
     └──────────────────────┘ └──────────────────────┘
           LRR 11                    LRR 12
```

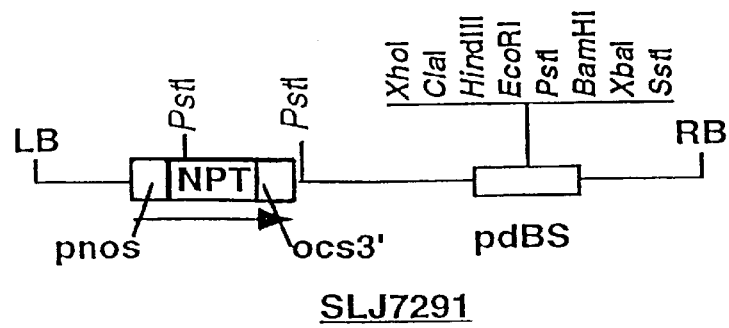
SLJ7291
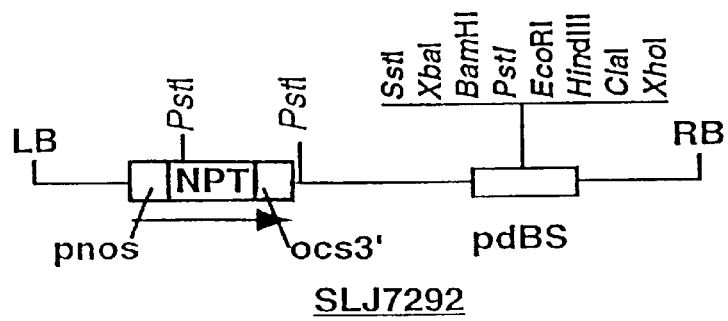
SLJ7292
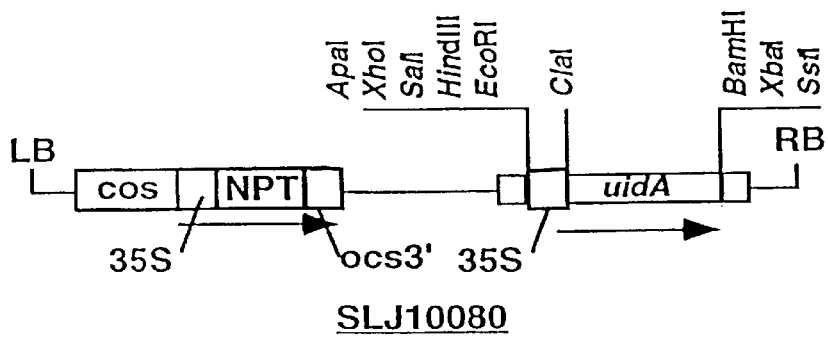
SLJ10080
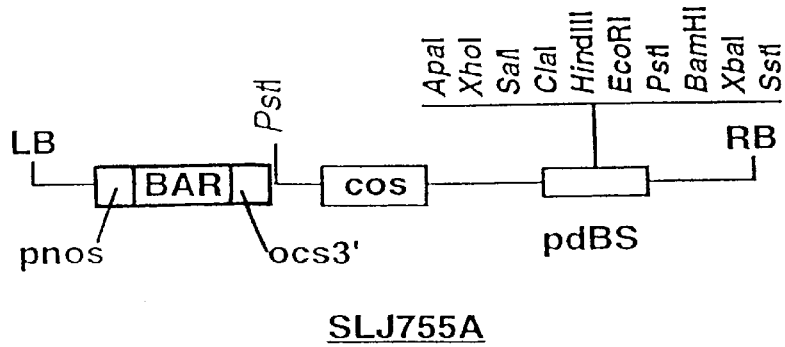
SLJ755A
Figure 9

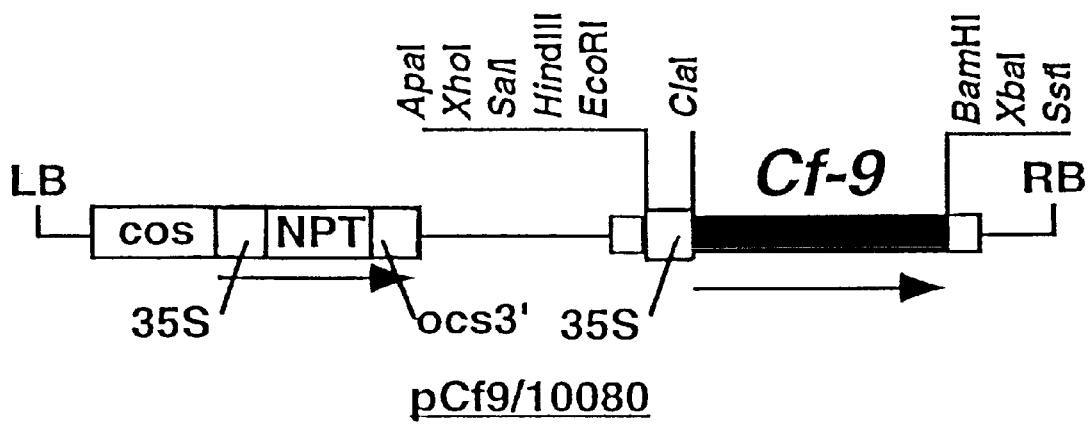
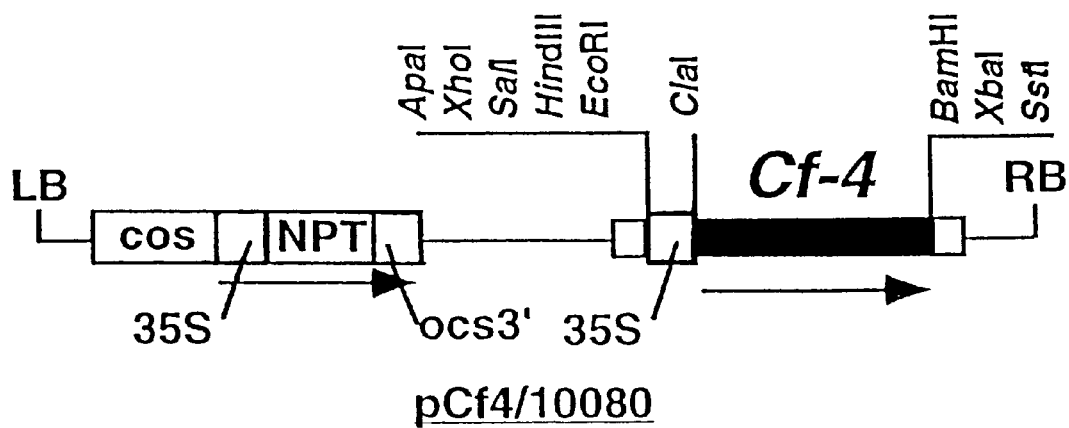
Figure 10

PLANT PATHOGEN RESISTANCE GENES AND USES THEREOF

The present invention relates to pathogen resistance in plants and more particularly the identification and use of pathogen resistance genes. It is based on cloning of the tomato Cf-4 gene.

Plants are constantly challenged by potentially pathogenic microorganisms. Crop plants are particularly vulnerable, since they are usually grown as genetically uniform monocultures. However, plants have evolved an array of both preexisting and inducible defences which pathogens must circumvent, especially those pathogens that derive their nutrition from an intimate association with living plant cells. If the pathogen can cause disease, the interaction is said to be compatible, but if the plant is resistant, the interaction is said to be incompatible.

Race specific resistance is often (though not exclusively) specified by dominant R genes. When pathogens mutate to overcome R genes, the mutations are often recessive. For R genes to function, there must also be a corresponding gene in the pathogen termed an avirulence gene (Avr). To become virulent, pathogens (fungi, bacteria or viruses) must no longer produce a product that triggers R gene-dependent defence mechanisms (Flor, 1971). One model, often termed the elicitor/receptor model, is that R genes encode products which enable plants to detect the presence of pathogens, provided the pathogen carries the corresponding Avr gene (Gabriel and Rolfe, 1990). This recognition is subsequently transduced into the activation of a defence response.

The characterization of two fungal avirulence genes from the tomato leaf mould pathogen *Cladosporium fulvum* has been reported. The Avr9 and Avr4 genes encode small cysteine rich peptides (van Kan et al., 1991; Joosten et al., 1995) which, in their mature processed forms, are composed of 28 and 106 amino acid residues respectively. Avr9 and Avr4 confer avirulence to races of *C. fulvum* on tomato lines carrying the R genes Cf-9 and Cf-4 respectively. We have shown that these two R genes are genetically tightly linked, or possibly allelic (Jones et al., 1993; Balint-Kurti et al., 1994). We isolated the Cf-9 gene by transposon tagging (Jones et al., 1994; PCT/GB94/02812, published as WO 95/18230) and we report here the positional cloning of Cf-4 using more refined genetic analysis and Cf-9 DNA as a probe. The availability of cloned avirulence genes and their cognate resistance genes may ultimately be exploited to engineer broad-based and durable disease resistance in a wide range of crop plants (de Wit, 1992; Staskawicz et al., 1995).

In plants gene isolation has been achieved by two main approaches, positional cloning and transposon tagging. Several plant genes have been successfully isolated by positional cloning (reviewed in Tanksley et al., 1995) including several R genes i.e. Pto (Martin et al., 1993) and Cf-2 from tomato (Dixon et al., 1996) and RPS2 and RPM1 from Arabidopsis (Bent et al., 1994; Mindrinos et al., 1994; Grant et al., 1995). Most positional cloning strategies have relied heavily on the use of restriction fragment length polymorphism (RFLP) markers. Recently however, PCR-based strategies have been developed which are capable of detecting more subtle DNA sequence variation allowing a much greater number of DNA sequences to be inspected for polymorphism. These techniques include random amplified polymorphic DNA (RAPDs, Williams et al., 1990) and amplified restriction fragment polymorphism analysis (AFLP, Zabeau and Vos, 1992, EP-A-92402629.7; Vos et al. 1995; Thomas et al., 1995) and should expedite plant gene isolation by positional cloning strategies. Transposon tagging has been used to isolate the N gene from tobacco (Whitham et al., 1994), $L^6$ from flax (Lawrence et al., 1995) and Cf-9 from tomato (Jones et al., 1994; PCT/GB94/02812, published as WO 95/18230).

Amino acid sequence comparisons of plant R genes has shown they currently constitute two major classes. All except PTO appear to contain leucine rich repeat (LRR) motifs but the R genes $L^6$, N, RPM1 and RPS2 appear to have additional domains not present in Cf-9 (Staskawicz et al., 1995) and Cf-2 (Dixon et al., 1996). Furthermore, $L^6$, N and RPS2 are probably located intracellularly in contrast to Cf-9 and Cf-2 which are composed largely of LRRs and are predicted to be predominantly extra-cytoplasmic membrane-anchored proteins. Our analysis shows that the predicted Cf-4 protein is highly homologous to Cf-9.

WO93/11241 reports the sequence of a gene encoding a polygalacturonase inhibitor protein (PGIP) that has some homology with Cf-9 and, as we have now discovered, Cf-4 (the subject of the present invention). Cf-9, Cf-4 and others (Cf-5, -2 etc.) are termed by those skilled in the art "pathogen resistance genes" or "disease resistance genes". PGIP-encoding genes are not pathogen resistance genes. A pathogen resistance gene (R) enables a plant to detect the presence of a pathogen expressing a corresponding avirulence gene (Avr). When the pathogen is detected, a defence response such as the hypersensitive response (HR) is activated. By such means a plant may deprive the pathogen of living cells by localised cell death at sites of attempted pathogen ingress. On the other hand, the PGIP gene of WO93/11241 (for example) is a gene of the kind that is induced in the plant defence response resulting from detection of a pathogen by an R gene.

Thus, a pathogen resistance gene may be envisaged as encoding a receptor to a pathogen-derived and Avr dependent molecule. In this way it may be likened to the RADAR of a plant for detection of a pathogen, whereas PGIP is involved in the defence the plant mounts to the pathogen once detected and is not a pathogen resistance gene. Expression of a pathogen resistance gene in a plant causes activation of a defence response in the plant. This may be upon contact of the plant with a pathogen or a corresponding elicitor molecule, though the possibility of causing activation by over-expression of the resistance gene in the absence of elicitor has been reported. The defence response may be activated locally, e.g. at a site of contact of the plant with pathogen or elicitor molecule, or systemically. Activation of a defence response in a plant expressing a pathogen resistance gene may be caused upon contact of the plant with an appropriate, corresponding elicitor molecule, e.g. as produced by a *Cladosporium fulvum* avr gene as discussed. The elicitor may be contained in an extract of a pathogen such as *Cladosporium fulvum*, or may be wholly or partially purified and may be wholly or partially synthetic. An elicitor molecule may be said to "correspond" if it is a suitable ligand for the R gene product to elicit activation of a defence response.

The "Cf-x"/"Avrx" terminology is standard in the art. The Cf resistance genes and corresponding fungal avirulence genes (Avr) were originally defined genetically as interacting pairs of genes whose measurable activities fall into mutually exclusive interacting pairs. Avr9 elicits a necrotic response on Cf-9 containing tomatoes but no response on Cf-4 containing tomatoes, the moeity recognised by Cf-4 being different from that recognised by Cf-9.

Expression of Cf-4 function in a plant may be determined by investigating compatibility of various *C. fulvum* races.

A race of *C. fulvum* that carries functional copies of all known Avr genes (race 0) will grow (compatible) only on a tomato which lacks all the Cf genes. It will not grow (incompatible) on a plant carrying any functional Cf gene. If the *C. fulvum* race lacks a functional Avr4 gene (race 4) it will be able to grow not only on a plant lacking any Cf genes but also a plant carrying the Cf-4 gene. A race also lacking a functional Avr2 gene (race 2,4) will also be able to grow on a plant carrying the Cf-2 gene. A race only lacking a functional Avr2 gene (race 2) will not be able to grow on a plant carrying Cf-4. Similarly, a *C. fulvum* race 5 (lacking a functional Avr5 gene) will not be able to grow on a plant carrying a Cf-4 gene. Neither a race 4 nor a race 2,4 will be able to grow on a plant carrying any of the other Cf genes. Various races are commonly available in the art, e.g. from the Research Institute for Plant Protection (IPO-DLO), PO Box 9060, 6700 GW Wageningen, The Netherlands. A race 4 is available under accession number IPO10379 and a race 2,4 available under Accession number IPO50379.

The Cf-2 gene is the subject of PCT/GB96/00785 filed Apr. 1, 1996 by John Innes Centre Innovations Limited and claiming priority from GB9506658.5.

We have now isolated a tomato gene, Cf-4, which confer resistance against the fungus *Cladosporium fulvum* and we have sequenced the DNA and deduced the amino acid sequence. The DNA sequence of the tomato Cf-4 gene is shown in FIG. 5 (SEQ ID NO. 1) and the deduced amino acid sequence shown in FIG. 6 (SEQ ID NO 2).

According to one aspect, the present invention provides a nucleic acid isolate encoding a pathogen resistance gene, the gene being characterized in that it encodes the amino acid sequence shown in SEQ ID No. 2, or a fragment thereof, or an amino acid sequence showing a significant degree of homology thereto. This may be a greater degree of sequence identity with the amino acid sequence of SEQ ID NO. 2 than is shown by the amino acid sequence of any of Cf-9, Cf-2 and Cf-5. This may be at least about 95% identity.

Most preferably the nucleic acid encodes the amino acid sequence shown in SEQ ID NO. 2 in which case the nucleic acid isolate may comprise nucleic acid having the sequence shown in SEQ ID No 1 or sufficient part to encode the desired polypeptide (eg from the initiating methionine codon to the first in frame downstream stop codon). In one embodiment DNA comprises a sequence of nucleotides which are the nucleotides 201 to 2618 of SEQ ID No. 1, or a mutant, derivative or allele thereof.

A further aspect of the invention provides a nucleic acid isolate encoding a pathogen resistance gene, or a fragment thereof, obtainable by screening a DNA library with a probe comprising nucleotides 201 to 2618 of SEQ ID No. 1, or a fragment, derivative, mutant or allele thereof, and isolating DNA which encodes a polypeptide able to confer pathogen resistance to a plant, such as resistance to races of *Cladosporium fulvum* (eg. expressing Avr4). The plant may be tomato. Suitable techniques are well known in the art.

Thus, the present invention also provides a method of identifying and/or isolating nucleic acid encoding a pathogen resistance gene comprising probing candidate (or "target") nucleic acid with nucleic acid which has a sequence of nucleotides which encodes an amino acid sequence shown in SEQ ID NO. 2, which is complementary to an encoding sequence or which encodes a fragment of either an encoding sequence or a sequence complementary to an encoding sequence. The candidate nucleic acid (which may be, for instance, cDNA or genomic DNA) may be derived from any cell or organism which may contain or is suspected of containing nucleic acid encoding a pathogen resistance gene. A preferred nucleotide sequence appears in SEQ ID NO. 1. Sequences complementary to the sequence shown, and fragments thereof, may be used.

Preferred conditions for probing are those which are stringent enough for there to be a simple pattern with a small number of hybridisations identified as positive which can be investigated further. It is well known in the art to increase stringency of hybridisation gradually until only a few positive clones remain.

Nucleic acid according to the present invention may encode the amino acid sequence shown in SEQ ID No. 2 or a mutant, derivative or allele of the sequence provided. Preferred mutants, derivatives and alleles are those which retain a functional characteristic of the protein encoded by the wild-type gene, especially the ability to confer pathogen resistance, and most especially the ability to confer resistance against a pathogen expressing the Avr4 elicitor molecule. Changes to a sequence, to produce a mutant or derivative, may be by one or more of insertion, deletion or substitution of one or more nucleotides in the nucleic acid, leading to the insertion, deletion or substitution of one or more amino acids. Of course, changes to the nucleic acid which make no difference to the encoded amino acid sequence are included.

Also provided by an aspect of the present invention is nucleic acid comprising a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a polypeptide able to confer pathogen resistance on a host, i.e. includes a pathogen resistance gene. Preferred conditions for hybridisation are familiar to those skilled in the art, but are generally stringent enough for there to be positive hybridisation between the sequences of interest to the exclusion of other sequences.

Nucleic acid according to the present invention, for instance mutants, derivatives and alleles of the specific sequences disclosed herein, may be distinguished from Cf-9, Cf-2 and/or Cf-5 by one or more of the following, or other features directly derivable from comparison of the Cf-4 amino acid sequence with the respective other sequence or by observation of gene function:

the amino acid sequence having at least about 95% identity with that of SEQ ID NO. 2;

eliciting a defence response, in a plant expressing the nucleic acid, upon contact of the plant with Avr4 elicitor molecule, e.g. as provided by a *Cladosporium fulvum* race expressing Avr4 (available in the art);

not eliciting a defence response, in a plant expressing the nucleic acid, upon contact of the plant with the *C. fulvum* race 4 deposited at and available from the Research Institute for Plant Protection (IPO-DLO), PO Box 9060, 6700 GW Wageningen, The Netherlands, under accession number IPO10379, or an extract thereof;

not eliciting a defence response in a plant expressing the.nucleic acid, upon contact of the plant with the *C. fulvum* race 2,4 deposited at and available from the same institute under Accession number IPO50379, or an extract thereof;

eliciting a defence response, in a plant expressing the nucleic acid, upon contact of the plant with Avr4 elicitor molecule, e.g. as provided by a *Cladosporium fulvum* race or other-organism expressing Avr4, amino acid and encoding nucleic acid sequences of which are given in WO95/31564 SEQ ID NO. 13, and FIG. 4 herein;

not eliciting a defence response, in a plant expressing the nucleic acid, upon contact of the plant with Avr9 elicitor molecule, e.g. as provided by a *Cladosporium fulvum* race or other organism expressing Avr9 (de Wit, 1992), the amino acid and encoding nucleic acid sequences of chimaeric forms of which are given for example in WO95/18230 as SEQ ID NO 3 and in WO95/31564 as SEQ ID NO 4;

not eliciting a defence response, in a plant expressing the nucleic acid, upon contact of the plant with Avr2 elicitor molecule, e.g. as provided by a *Cladosporium fulvum* race or other organism expressing Avr2;

not eliciting a defence response, in a plant expressing the nucleic acid, upon contact of the plant with Avr5 elicitor molecule, e.g. as provided by a *Cladosporium fulvum* race or other organism expressing Avr5;

eliciting a defence response, in a plant expressing the nucleic acid and a corresponding elicitor molecule, at an earlier developmental stage than the defence response elicited in such a plant expressing the Cf-9 gene and corresponding Avr9 molecule;

eliciting a defence response in a non-photosynthetic tissue (e.g. root) of a plant expressing the nucleic acid, upon contact of the plant with corresponding elicitor molecule, such as Avr4;

comprising the number of leucine rich repeats (LRR's) identifiable from the sequence information provided herein for Cf-4.

The Cf-4 polypeptide, and others such as Cf-9, Cf-2 and Cf-5, may be distinguished from the products of other pathogen resistance genes by being putative transmembrane proteins. The gene product of the Arabidopsis RPP5 gene, for example, is a putative cytoplasmic protein.

A nucleic acid isolate according to the invention may encode a pathogen resistance gene whose expression in a plant can cause activation of a defence response in the plant, comprising a sequence of nucleotides encoding a polypeptide comprising the sequence of amino acids shown in SEQ ID NO. 2.

The activation may be upon contact of the plant with a pathogen or corresponding elicitor molecule.

The sequence of nucleotides may comprise an encoding sequence shown in SEQ ID NO. 1. For example, the sequence may comprise nucleotides 201–2619 of SEQ ID NO. 1.

The nucleic acid may include a sequence of nucleotides comprising an allele, derivative or mutant, by way of addition, insertion, deletion or substitution of one or more nucleotides, of an encoding sequence shown in SEQ ID NO. 1.

Nucleic acid according to the present invention may encode a pathogen resistance gene whose expression in a plant can cause activation of a defence response in the plant, comprising a sequence of nucleotides encoding a polypeptide, the polypeptide comprising an amino acid sequence which comprises an allele, derivative or mutant, by way of addition, insertion, deletion or substitution of one or more amino acids, of the amino acid sequence shown in SEQ ID NO. 2.

The nucleic acid isolate, which may contain the DNA encoding the amino acid sequence of SEQ ID No. 2 or an amino acid sequence showing a significant degree of homology thereto as genomic DNA or cDNA, may be in the form of a recombinant vector, for example a phage or cosmid vector. The DNA may be under the control of an appropriate promoter and regulatory elements for expression in a host cell, for example a plant cell. In the case of genomic DNA, this may contain its own promoter and regulatory elements and in the case of genomic DNA this may be under the control of an appropriate promoter and regulatory elements for expression in the host cell.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual*: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al., along with all other documents cited in the present text are incorporated herein by reference.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may comprise cDNA, RNA, genomic DNA and may be wholly or partially synthetic. The term "isolate" encompasses all these possibilities.

When introducing a chosen gene construct into a cell, certain considerations must be taken into account, well known to those skilled in the art. The nucleic acid to be inserted may be assembled within a construct which contains effective regulatory elements to promote transcription. There must be available a method of transporting the construct into the cell. Once the construct is within the cell membrane, integration into the endogenous chromosomal material may or may not occur according to different embodiments of the invention. Finally, as far as plants are concerned the target cell type should be such that cells can be regenerated into whole plants.

Plants transformed with the DNA segment containing pre-sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, Bevan, 1984), particle or microprojectile bombardment (U.S. Pat. No. 5100792, EP-A-444882, E-A-434616) microinjection (WO 92/09696, WO 94/00583, EP 331083, EP 175966), electroporation (EP 290395, WO 8706614) or other forms of direct DNA uptake (DE 4005152, WO 9012096, U.S. Pat. No. 4684611). Agrobacterium transformation is widely used by those skilled in the art to transform dicotyledonous species. Although Agrobacterium has been reported to be able to transform foreign DNA into some monocotyledonous species (WO 92/14828), microprojectile bombardment, electroporation and direct DNA uptake are preferred where Agrobacterium is inefficient or ineffective. Alternatively, a combination of different techniques may be employed to enhance the efficiency of the transformation process, eg. bombardment with Agrobacterium coated microparticles (EP-A-486234) or microprojectile bombardment to induce wounding followed by co-cultivation with Agrobacterium (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention.

A Cf-4 gene and modified versions thereof, e.g. encoding a protein showing a significant degree of homology to the protein product of the Cf-4 gene, alleles, mutants and derivatives thereof, may be used to confer resistance in plants, in particular tomatoes, to a pathogen such as *C. fulvum*. This may include cloned DNA from *Lycopersicon hirsutum* which has the same chromosomal location as the Cf-4 gene or any subcloned fragment thereof. For this purpose a vector as described above may be used for the production of a transgenic plant. Such a plant may possess pathogen resistance conferred by the Cf-4 gene.

The invention thus further encompasses a host cell transformed with such a vector, especially a plant or a microbial cell. Thus, a host cell, such as a plant cell, comprising nucleic acid according to the present invention is provided. Within the cell, the nucleic acid may be incorporated within the chromosome.

A vector comprising nucleic acid according to the present invention need not include a promoter, particularly if the vector is to be used to introduce the nucleic acid into cells for recombination into the genome.

Also according to the invention there is provided a plant cell having incorporated into its genome a sequence of nucleotides as provided by the present invention, under operative control of a promoter for control of expression of the encoded polypeptide. A further aspect of the present invention provides a method of making such a plant cell involving introduction of a vector comprising the sequence of nucleotides into a plant cell. Such introduction may be followed by recombination between the vector and the plant cell genome to introduce the sequence of nucleotides into the genome. The polypeptide encoded by the introduced nucleic acid may then be expressed.

A plant which comprises a plant cell according to the invention is also provided, along with any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on.

The invention further provides a method of comprising expression from nucleic acid encoding the amino acid sequence SEQ ID No. 2, or a mutant, allele or derivative thereof, or a significantly homologous amino acid sequence, within cells of a plant (thereby producing the encoded polypeptide), following an earlier step of introduction of the nucleic acid into a cell of the plant or an ancestor thereof. Such a method may confer pathogen resistance on the plant. This may be in combination with the Avr4 gene according to any of the methods described in WO91/15585 (Mogen) or, more preferably, PCT/GB95/01075, published as WO95/31564, or any other gene involved in conferring pathogen resistance.

The Cf-4, Cf-9 and Cf-2 genes function in a similar manner in that they confer resistance to tomato that prevents growth of the tomato leaf mould *C. fulvum*. They do, however, work by the recognition of different Avr products and have subtle differences in the speed with which they stop growth of the pathogen and stimulate a resistance response (Hammond-Kosack and Jones 1994, Ashfield et al. 1994). These differences may be exploited to optimise applications disclosed herein and in Wo 95/31564 (above).

A gene stably incorporated into the genome of a plant is passed from generation to generation to descendants of the plant, cells of which decendants may express the encoded polypeptide and so may have enhanced pathogen resistance. Pathogen resistance may be determined by assessing compatibility of a pathogen (eg. *Cladosporium fulvum*) or using recombinant expression of a pathogen avirulence gene, such as Avr-4 or delivery of the Avr-4 gene product, for example in the form of a recombinant virus as described herein.

Sequencing of the Cf-4 gene has shown that like the Cf-9 gene (PCT/GB94/02812; Jones et al., 1994) and Cf-2 (PCT/GB96/00785; Dixon et al., 1996) it includes DNA sequence encoding leucine-rich repeat (LRR) regions and homology searching has revealed strong homologies to other genes containing LRRs. All three genes exhibit similar general features and as such represent a new class of disease resistance genes separate from other disease resistance genes characterised to date.

According to a further aspect, the present invention provides a method of identifying a plant pathogen resistance gene comprising use of an oligonucleotide which comprises a sequence or sequences that are conserved between pathogen resistance genes, such as Cf-9 and Cf-4, and/or Cf-4 and Cf-2, to search for new resistance genes. Thus, a method of obtaining nucleic acid comprising a pathogen resistance gene (encoding a polypeptide able to confer pathogen resistance) is provided, comprising hybridisation of an oligonucleotide (details of which are discussed herein) or a nucleic acid molecule comprising such an oligonucleotide to target/candidate nucleic acid. Target or candidate nucleic acid may, for example, comprise a genomic or cDNA library obtainable from an organism known to encode a pathogen resistance gene. Clones that hybridise may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

As anbalternative to probing, though still employing nucleic acid hybridisation, oligonucleotides designed to amplify DNA sequences may be used in PCR is reactions or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between polypeptides able to confer pathogen resistance, such as those encoded by Cf-4 and Cf-9, and/or Cf-4 and Cf-2 and/or Cf-4, Cf-9 and Cf-2.

On the basis of amino acid sequence information, oligonucleotide probes or primers may be designed, taking into account the degeneracy of the genetic code, and, where appropriate, codon usage of the organism from the candidate nucleic acid is derived.

Preferably an oligonucleotide in accordance with the invention, e.g. for use in nucleic acid amplification, has about 10 or fewer codons (e.g. 6, 7 or 8), i.e. is about 30 or fewer nucleotides in length (e.g. 18, 21 or 24).

Assessment of whether or not a PCR product corresponds to a resistance gene may be conducted in various ways. A PCR band may contain a complex mix of products. Individual products may be cloned and each screened for linkage to known disease resistance genes that are segregating in progeny that showed a polymorphism for this probe. Alternatively, the PCR product may be treated in a way that enables one to display the polymorphism on a denaturing polyacrylamide DNA sequencing gel, with specific bands that are linked to the resistance gene being preselected prior to cloning. Once a candidate PCR band has been cloned and shown to be linked to a known resistance gene, it may be used to isolate clones which may be inspected for other features and homologies to Cf-9, Cf-2, Cf-4 or other related gene. It may subsequently be analysed by transformation to assess its function on introduction into a disease sensitive variety of the plant of interest. Alternatively, the PCR band or sequences derived by analysing it may be used to assist plant breeders in monitoring the segregation of a useful resistance gene.

These techniques are of general applicability to the identification of pathogen resistance genes in plants. Examples of the type of genes that can be identified in this way include Phytophthora resistance in potatoes, mildew resistance and rust resistance in cereals such as barley and maize, rust resistance in Antirrhinum and flax, downy mildew resistance in lettuce and Arabidopsis, virus resistance in potato, tomato and tobacco, nematode resistance in tomato, resistance to bacterial pathogens in Arabidopsis and tomato and Xanthomonas resistance in peppers.

Once a pathogen resistance gene has been identified, it may be reintroduced into plant cells using techniques well known to those skilled in the art to produce transgenic plants. According to a further aspect, the present invention provides a DNA isolate encoding the protein product of a plant pathogen resistance gene which has been identified by use of the presence therein of LRRs or, in particular, by the technique defined above.

According to yet a further aspect, the invention provides transgenic plants, in particular crop plants, which have been engineered to carry pathogen resistance genes which have been identified by the presence of LRRs or by nucleic acid hybridisation as disclosed.

Examples of plants according to the present invention include tobacco, cucurbits, carrot, vegetable brassica, lettuce, strawberry, oilseed brassica, sugar beet, wheat, barley, maize, rice, soyabeans, peas, sorghum, sunflower, tomato, potato, pepper, chrysanthemum, carnation, poplar, eucalyptus and pine.

Modifications to and further aspects and embodiments of the invention will be apparent to those skilled in the art. All documents mentioned herein are incorporated by reference. The term "comprises" should be interpreted herein as meaning "includes" or "has", not "consists of".

As already indicated, the present invention is based on the cloning and sequencing of the tomato Cf-4 genes and this experimental work is described in more detail below with reference to the following figures.

FIG. 1 shows a Southern blot of BglII digested DNA isolated from near isogenic lines (NILs) of L. esculentum cv. Moneymaker containing either the Cf-9 (Cf9) or Cf-4 (Cf4) resistance genes, a line containing no known resistance genes to C. fulvum (Cf0), and another line (Cf1, L. esculentum cv. Stirling Castle) containing the Cf-1 resistance gene which has also been mapped to the short arm of tomato chromosome 1. The location of the 6.7 kbp BglII band corresponding to the Cf-9 gene and 3 BglII bands specific to Cf-4 containing lines and described in the text, are also shown.

Figure 2:
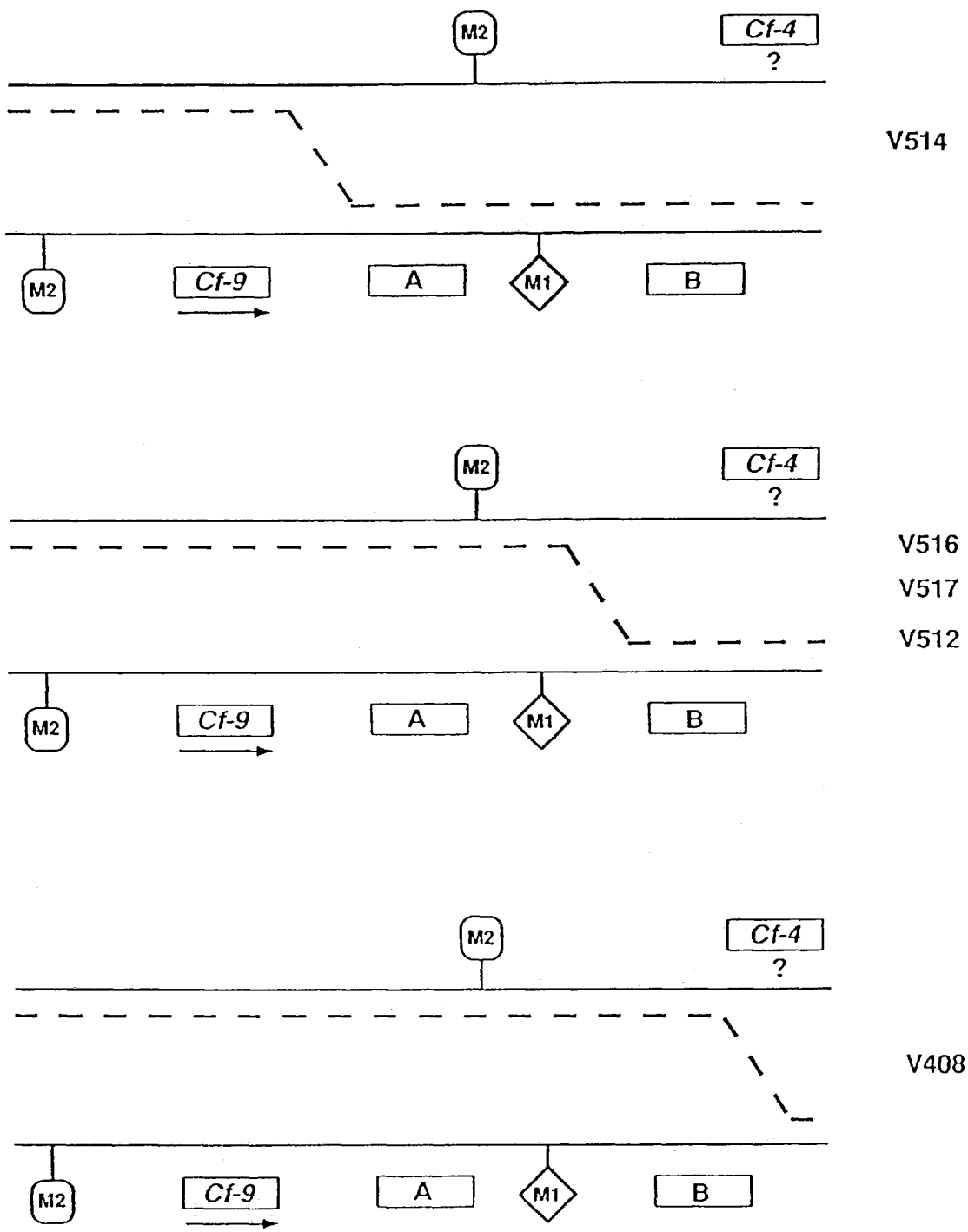

FIG. 2 shows in schematic form the three classes of recombinants identified in our analysis of 5 disease-sensitive recombinants (V408, V512, V514, V516 and V517) from the Cf-4/Cf-9 transheterozygote testcross population. The Cf-4 locus is depicted on the upper line and Cf-9 on the lower line. The location of two AFLP markers which flank Cf-9 (M1 and M2, Thomas et al., 1995) are shown; one of these markers (M2) is also present at the Cf-4 locus. Two other members of the multigene family located distal to Cf-9 (shown here as genes A and B) which are present in some disease-sensitive recombinants are also shown. Recombination breakpoints in each of the 3 classes which have been deduced by Southern hybridization and AFLP analysis are represented by broken lines.

Figure 3:
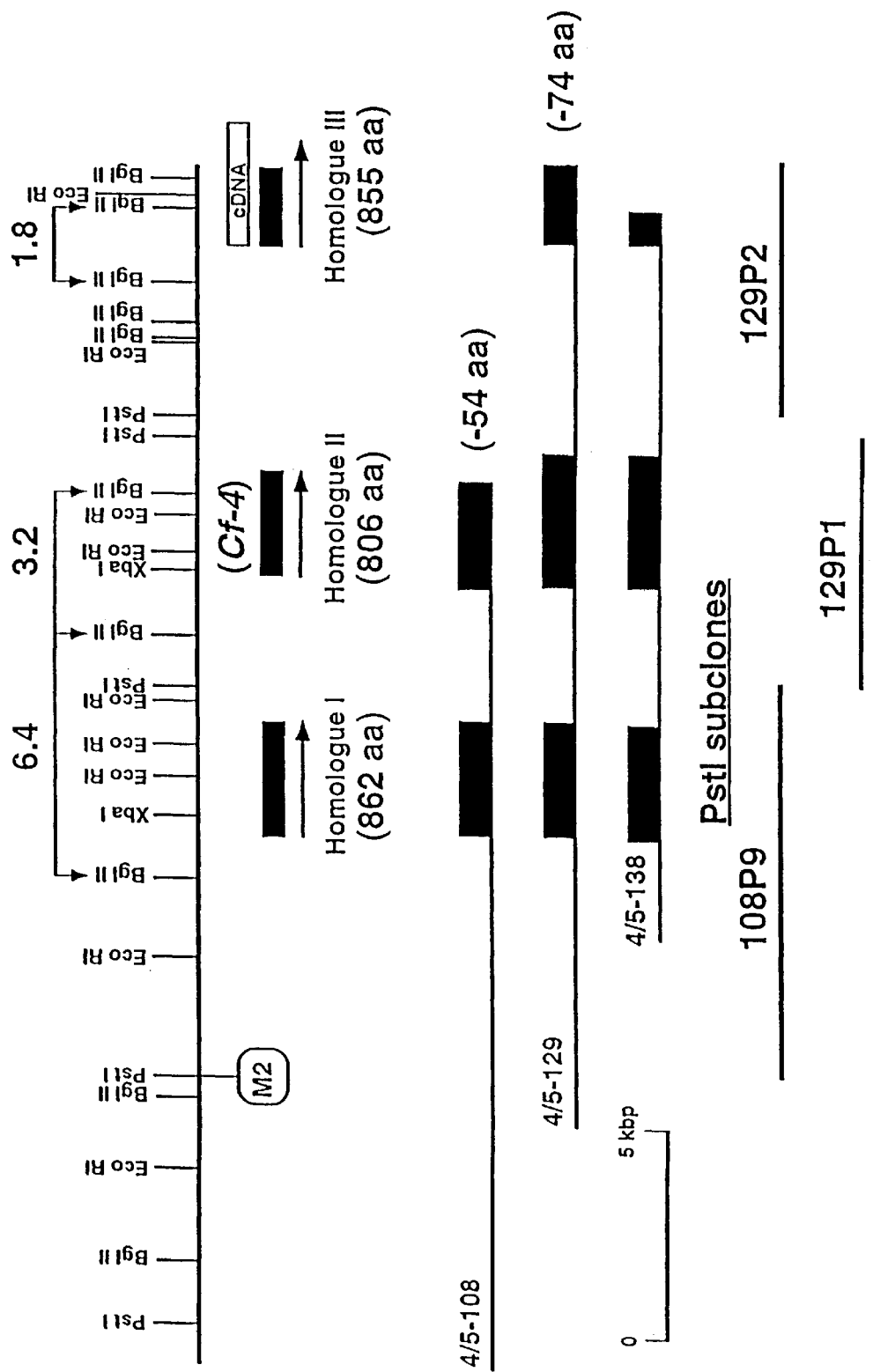

FIG. 3 shows a physical map of the Cf-4 locus deduced from 3 overlapping cosmids (4/5-108, 4/5-129 and 4/5-138) isolated from the Cf-4/Cf-5 cosmid library. The physical extent of each cosmid is shown schematically and the location of 3 Cf-9 homologous sequences determined by hybridization and sequence analysis are represented by black boxes. The transcriptional polarity of each gene is indicated by an arrow. The location of the Cf-4 gene is also shown. Restriction enzyme sites for the following enzymes are also indicated; BglII, PstI, EcoRI and XbaI. The location of the 3 BglII fragments (6.4 kbp, 3.2 kbp and 1.8 kbp) showing high homology to a probe derived from the 5' end of Cf-9 (see FIG. 1) are indicated by arrows. M2 represents an AFLP marker originally identified at the Cf-9 locus also present at the Cf-4 locus.

FIG. 4 shows the nucleic acid (in double-stranded form) (SEQ ID NO:3 and SEQ ID NO:5) and deduced amino acid sequence (SEQ ID NO:4) of a ClaI/SalI DNA fragment encoding the PR1a signal peptide sequence fused to a sequence proposed to encode the mature processed form of C. fulvum AVR4. Translation initiation codon at nucleotide 5, termination codon beginning at nucleotide 413. Amino acids 1–30 represent the signal peptide sequence and amino acids 31–136 the mature AVR4 peptide.

FIG. 5 shows a genomic DNA sequence of Cf-4 (SEQ ID No. 1). Features of the sequence include; translation start site at nucleotide 201; translation stop beginning at nucleotide 2619; consensus polyadenylation sequence (AATAAA) beginning at nucleotide 2835; splice donor sequence in 3' untranslated sequence at nucleotide 2641; splice acceptor sequence ending at nucleotide 2755; proposed site of polyadenylation at nucleotide 2955.

FIG. 6 shows the predicted amino acid sequence of the Cf-4 gene (SEQ ID NO 2) according to the single letter amino acid code. The predicted protein sequence is composed of a primary translation product of 806 amino acids; signal peptide sequence amino acids 1–23; mature peptide amino acids 24–806.

FIGS. 7A–7G show the seven proposed structural domains A–G of the Cf-4 protein as described for Cf-9 by Jones et al. (1994) and discussed in the text. Deletions in Cf-4 relative to Cf-9 are indicated by a dot. The majority of amino acids which distinguish the two proteins are located in their respective N-termini and are indicated in the figure as bold characters. Potential N-glycosylation sequences are shown underlined.

FIGS. 8A and 8B show the two regions of major sequence divergence between the Cf-4 and Cf-9 sequences. (FIG. 8A) Alignment of Cf-9 amino acids 40–79 of domain B (upper line) with amino acids 40–69 of Cf-4 (lower line). (FIG. 8B) Alignment of Cf-9 amino acids 285–426 (LRRs 9–14) with amino acids 274–369 of Cf-4 (LRRs 9–12).

FIG. 9 shows the structure of four binary vector plasmids used extensively for the expression of transgenes reported here. LB and RB correspond to the left and right borders of the T-DNA in each vector. Plant transformation marker genes were located at the LB end and were either the neomycin phosphotransferase gene (NPT) or a gene from *Streptomyces hygroscopicus* conferring resistance to phosphinotricin (BAR). Transformation marker genes were either under control of the cauliflower mosaic virus 35S promoter (35S) or the nopaline synthase gene promoter from *A. tumefaciens* (pnos). Transcription termination signals were provided by the *A. tumefaciens* octopine synthase gene 3' sequence (ocs3'). SLJ7291, SLJ7292 and SLJ755A all contain polylinker sequences with sites for the restriction enzymes indicated in the figure. The polyliner sequence was derived from a modified pBluescript plasmid as described by Jones et al. (1992). The transcriptional orientation of all genes is indicated by an arrow. All manipulations were performed as described by Jones et al. (1992). SLJ10080 was derived from the binary cosmid vector pCLD04541 by removing the ClaI site in the polylinker sequence by linearization with ClaI, T4 DNA polymerase treatment and self ligation. The 35S:uidA cassette from SLJ4K1 was cloned into the resulting plasmid as an EcoRI/BamHI fragment. Cf-4 and Cf-9 coding sequences for transient expression studies were cloned in as ClaI/BamHI fragments replacing the uida gene (see FIG. 10). Plasmids SLJ755A and pCLD04541, and their derivatives, contain a lambda phage sequence (cos) for use as cosmid cloning vectors.

FIG. 10 binary vectors for expression of Cf-9 (pCf9/10080) and Cf-4 (pCf4/10080) in transient assays. See text for details of each construct.

Figure 11:
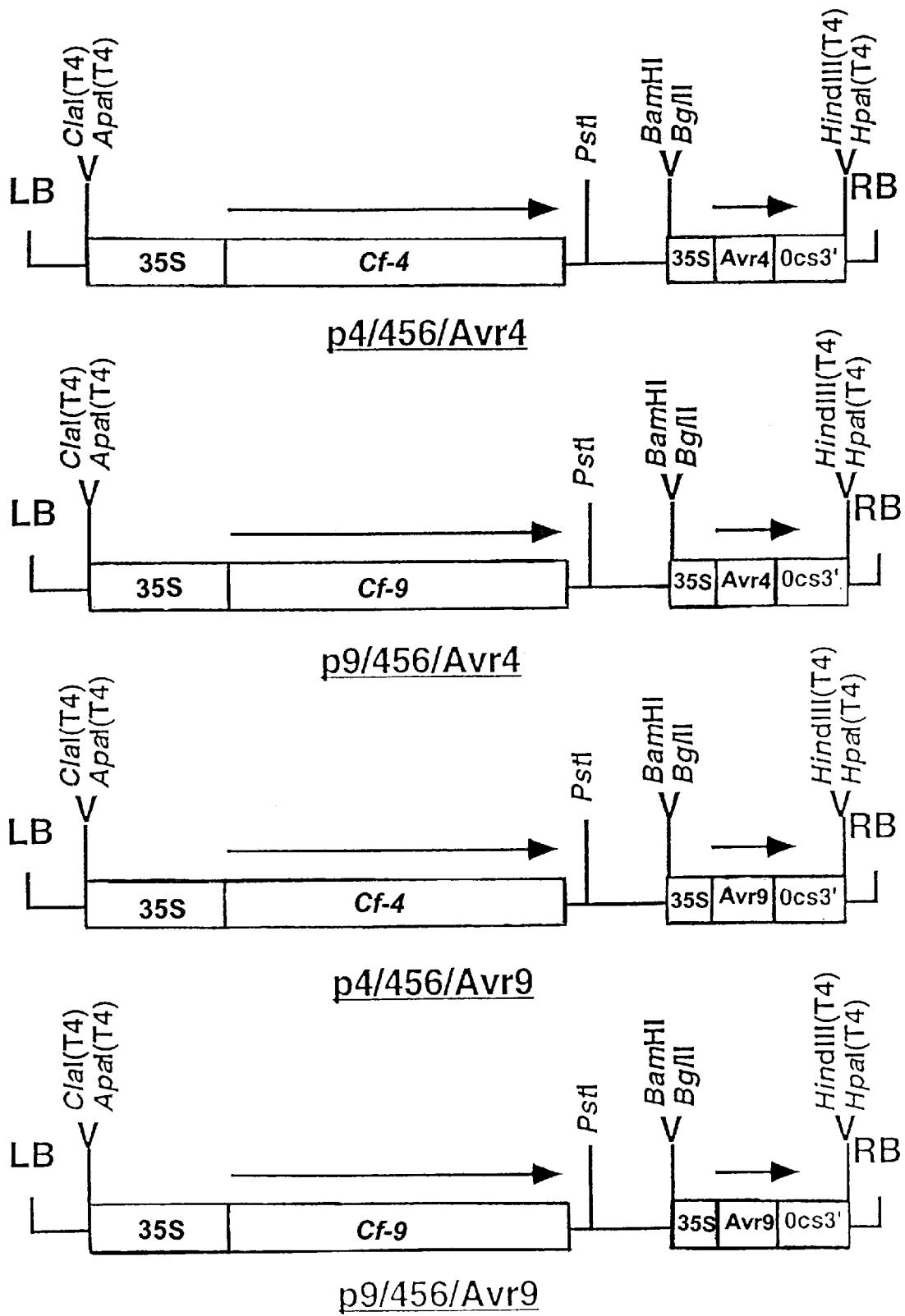

FIG. 11 four binary constructs containing either Cf-9 or Cf-4 genes under control of the 35S promoter (35S), in combination with either of the *C. fulvum* avirulence genes Avr9 or Avr4. Avirulence genes were also under control of the 35S promoter; transcription termination sequences were provided by the *A. tumefaciens* octopine synthase gene 3' untranslated region (ocs3'). Only restriction enzyme sites relevant to the construction of each plasmid (see text for details) are shown.

POSITIONAL CLONING OF THE TOMATO Cf-4 GENE (1) Cf-4 Map Location.

We have mapped several genes conferring resistance to *C. fulvum* on the classical and RFLP maps of tomato (Dickinson et al., 1993; Jones et al., 1993; Balint-Ku-ti et al., 1994; Thomas et al., 1995). These studies demonstrated that Cf-4 and Cf-9 map to a similar location within a 6 cM interval delimited by two RFLP markers CP46 and TG236 on the short arm of chromosome 1. Cf-4 and Cf-9 have been introgressed into cultivated tomato from its wild relatives *L. hirsutum* and *L. pimpinellifolium* respectively (see Jones et al., 1993). Our genetic analysis suggests these genes are tightly linked, or possibly allelic. We have isolated Cf-9 by transposon tagging using the maize transposon Dissociation (Jones et al., 1994; PCT/GB/02812) and this has enabled us to isolate Cf-4 by positional cloning.

(2) Identification of Candidate Cf-4 Genes.

DNA from NILs of tomato containing Cf-9, Cf-4 or no known resistance genes to *C. fulvum* were isolated and digested with restriction enzyme BglII. Southern hybridization analysis with the probe pCf9XS encompassing the 5' end of Cf-9 (Jones et al., 1994) revealed extensive RFLPs between the 3 lines (FIG. 1). This result was predicted since these resistance genes have been introgressed from different species and since multiple members of this gene family are present on the same introgressed chromosomal segment.

In order to identify a candidate Cf-4 gene we intercrossed the Cf4 and Cf9 NILs to generate a Cf-4/Cf-9 transheterozygote. Progeny were subsequently crossed to Cf0 to generate an $F_1$ test cross population. Approximately 7,500 progeny were inoculated with *C. fulvum* race 5 which is incompatible on plants containing either Cf-4 or Cf-9. We reasoned that if Cf-4 and Cf-9 are allelic genes, intragenic recombination could occur in the transheterozygous parent, albeit at a low frequency. In some cases this might remove the resistance specificities of each gene. Progeny containing such recombinant chromosomes would be detected in our analysis as disease-sensitive individuals.

Alternatively, if Cf-4 and Cf-9 are not allelic but only closely linked, intergenic recombination could occur, again at low frequency, to generate recombinants either containing both resistance genes or neither. These latter recombinant classes could also be generated as a consequence of chromosomal mis-pairing at meiosis and unequal crossing over. In our analysis only progeny lacking Cf-4 and Cf-9 were identified. Five such disease-sensitive recombinants were detected in 7,500 test cross progeny. These individuals were self-pollinated and progeny were again tested with *C. fulvum* race 5 to confirm they had lost both Cf-4 and Cf-9. Progeny were also identified which were homozygous for the recombinant chromosome. This was performed to simplify subsequent Southern hybridization analysis and was achieved by identifying individuals homozygous for the Cf9 allele of the RFLP marker CP46 located 2.5 cM distal to Cf-9 (Balint-Kurti et al., 1994; Thomas et al., 1995).

Southern hybridization analysis of BglII digested DNA from the 5 disease-sensitive individuals (V408, V512, V514, V516 and V517) using pCf9XS as probe confirmed that as predicted, all lacked the 6.7 kilobasepair (kbp) BglII band corresponding to the Cf-9 gene (Jones et al., 1994) and a number of other bands located proximal to the gene. Two other BglII bands comprising different members of this gene family and located distal to Cf-9 were present in some recombinants but not others (FIG. 2). Three BglII bands present in Cf-4 containing lines (6.4 kbp, 3.2 kbp and 1.8 kbp, FIG. 1) were also consistently absent from disease-sensitive individuals and were thus candidates for the Cf-4 gene. This latter result is consistent with analysis of $F_2$ plants from the cross Cf4×*L. pennellii*. Specific classes of $F_2$ individuals recombinant in the TG236/CP46 interval were identified by PCR analysis of leaf material as described previously (Balint-Kurti et al., 1994; Thomas et al., 1995). These results demonstrated the 3 BglII restriction fragments cosegregate with Cf-4. Using Southern hybridization and AFLP analysis we could distinguish 3 classes of recombinants which are depicted in FIG. 2. These results are consistent with, but not proof of, a model of chromosomal mis-pairing and unequal crossing over to generate recombinant chromosomes lacking both Cf-4 and Cf-9.

(3) Isolation of Binary Vector Cosmid Clones Containing Cf-9 Homologous Sequences.

A genomic DNA library was constructed from a stock that carried both the Cf-4 gene on chromosome 1, and the Cf-5 gene on chromosome 6, so that the library could be used for isolating both genes. The library was constructed in a binary cosmid cloning vector pCLD04541, obtained from Dr C. Dean at the John Innes Centre, Norwich (see Bent et al., 1994). The use of such a cloning vector is advantageous since any clones that are isolated can be introduced directly into plants to test for the function of the cloned gene.

High molecular weight DNA was isolated from leaves of 6 week old greenhouse-grown plants by techniques well known to those skilled in the art (Thomas et al., 1994) and partially digested with MboI restriction enzyme. The partial digestion products were size fractionated using a sucrose gradient and DNA in the size range 20–25 kbp was ligated to BamHI digested pCLD04541 DNA, using techniques well known to those skilled in the art. After in vitro packaging using Stratagene packaging extracts, the cosmids were introduced into a tetracycline sensitive version of *Escherichia coli* strain SURE™ (Stratagene). Recombinants were selected using the tetracycline resistance gene on pCLD04541.

The library was randomly distributed into 144 pools containing about 1500 clones per pool, cells were grown from each pool and from 10 ml of cells, 9 ml were used for bulk plasmid DNA extractions, and 1 ml was used after addition of 0.2 ml of glycerol, to prepare a frozen stock. Plasmid DNA from the pools was isolated by alkaline lysis (Birnboim and Doly, 1979), and DNA samples were subjected to PCR analysis using the primers F7 and F10 which were used to amplify the pCf9XS fragment from a Cf-9 containing tomato line (Jones et al., 1994). Pools 108, 129 and 138 from this library were identified as positive pools for the F7/F10 PCR product. For each pool, approximately 10,000 colonies were plated out and probed by colony hybridisation with radioactively labelled pCf9XS. From each pool, single homologous clones were isolated. These techniques are well known to those skilled in the art.

The 3 cosmid clones designated 4/5-108, 4/5-129 and 4/5-138 were further characterized by Southern blot hybridisation using pCf9XS as probe and by restriction enzyme mapping. The physical relationships of the 3 cosmids are shown in FIG. 3. This analysis showed there were 3 regions showing high homology with pCf9XS located on BglII restriction fragments of 6.4, 3.2 and 1.8 kbp consistent with results described previously (FIGS. 1 and 2). These 3 regions were subcloned as PstI fragments from the appropriate cosmid clones (FIG. 3) and their DNA sequences determined using techniques well known to those skilled in the art, with oligonucleotide primers previously used to determine the Cf-9 genomic sequence (Jones et al., 1994) in addition to some new primers specific for each of the 3 homologues. The DNA sequences of Homologues I and II were determined entirely from PstI clones derived from cosmids 4/5-108 and 4/5-129 respectively. DNA sequence analysis of a PstI fragment from cosmid 4/5-129 encompassing Homologue III suggested this cosmid does not contain a complete copy of this gene. Physical mapping data suggests this sequence is truncated to a greater extent on cosmid 4/5-138 (FIG. 3). This interpretation was confirmed by DNA sequence analysis of a cDNA clone of Homologue III isolated from a Cf-4/Cf-5 cDNA library. This analysis showed that the copy of Homologue III on cosmid 4/5-129 was truncated by 74 amino acids at its C-terminus. The predicted amino acid sequences of Homologue I (862 amino acids) Homologue II (806 amino acids) and Homologue III (855 amino acids) all show high levels of homology to Cf-9 (86.5%, 91.5% and 86.5% identical amino acids respectively).

(4) Development of an Efficient Assay for Cf-4 Gene Function in Plants.

The function of a putative cloned Cf-4 gene in transgenic plants can be assessed in a number of ways; firstly by inoculation with a race of *C. fulvum* containing the corresponding avirulence gene Avr4 to test if that race gives an incompatible response on the transgenic plant; secondly by injecting leaves of a transformed plant with intercellular fluid isolated from a compatible interaction containing AVR4; thirdly, by delivering AVR4 in the form of recombinant potato virus X as described previously in studies of the Cf-9/AVR9 interaction (Hammond-Kosack et al., 1995).

The DNA sequence of the *C. fulvum* gene encoding AVR4 has been reported and the amino acid sequence of the mature processed polypeptide (Joosten et al., 1994). We amplified by PCR the Avr4 gene from *C. fulvum* race 2,5 using primers to the published sequence and fused a sequence encoding the proposed mature polypeptide to a DNA sequence encoding the N-terminal signal peptide of the tobacco PRla protein. This would facilitate targeting of AVR4 to the intercellular space in transgenic plants where it is expressed. This chimeric gene (SPAvr4) was inserted into a cDNA copy of potato virus X, as a ClaI/SalI DNA fragment (FIG. 4) as described previously (Hammond-Kosack et al.,1995) to generate PVX:SPAvr4. Infectious transcripts of the recombinant virus were generated by in vitro transcription. All nucleic acid manipulations were performed using standard techniques well known to those skilled in the art.

Control experiments were designed to test the recombinant virus in 3 week old tomato seedlings. In Cf-4 containing plants inoculated cotyledons appeared desiccated and eventually abscised at 3 days post-inoculation (d.p.i.), in contrast to Cf0 controls which only showed.signs of slight mechanical damage at the site of virus inoculation. CfO plants developed visible symptoms of virus infection at 7–10 d.p.i. comparable to symptoms observed with the wild type virus i.e. chlorotic mosaic symptoms. At 4–5 d.p.i. in plants containing Cf-4 necrotic lesions were observed in the younger leaves presumably due to systemic spread of the virus as described previously in similar experiments with PVX containing Avr9 on Cf-9 containing plants (Hammond-Kosack et al., 1995). Other features included necrotic sectors on petioles and the stem. The necrotic phenotype was seen to spread systemically and at 14 d.p.i. the majority of Cf-4 containing seedlings had died. Cf0 control plants did not die but did show symptoms of chlorosis and vein-clearing. This procedure therefore, provides a rapid and reliable assay for Cf-4 function in plants and was applied to transgenic plants to identify individuals potentially carrying the Cf-4 gene.

(5) Identification of Binary Vector Cosmid Clones Containing a Genomic Copy of the Cf-4 Gene.

To test if any of the 3 binary vector cosmid clones (4/5-108, 4/5-129 and 4/5-138) isolated from the Cf-4/Cf-5 binary vector cosmid library contained Cf-4, transgenic tomato (*Lycopersicon esculentum*) and tobacco (*Nicotiana tabacum* cv Petite Havana) plants were produced (Fillatti et al.,1987; Horsch et al., 1985) using techniques well known to those skilled in the art.

Transgenic plants were propagated by cuttings so that Cf-4 activity could be detected by inoculation with PVX:SPAvr4 on 12 tomato transformants. No transgenic tomato plants (0/3) containing cosmid 4/5-108 exhibited PVX:SPAvr4 dependent leaf necrosis. In contrast, 6 out of 8 transformants containing cosmid 4/5-129 and 3 out of 4 containing cosmid 4/5-138 did exhibit leaf necrosis on inoculated leaves 3–4 d.p.i. (Table 1). This necrosis eventually spread systemically as previously observed in Cf-4 control plants. Transgenic plants exhibiting necrotic leaf sectors eventually died. Cuttings of a number of transgenic plants obtained in the first round of transformation experiments were further assayed for Cf-4 function by inoculation with C. fulvum race 5 (Table 1).

In these tests a positive correlation was observed between transgenic plants exhibiting PVX:SPAVR4 dependent necrosis and ones resistant to Cladosporium fulvum race 5 (Table 1). Pathogen growth was observed on compatible control plants (Cf0) but not on incompatible control plants (Cf2). Self progeny of several transgic were again tested with C. fulvum race 5 to confirm that the trait was heritable. This was shown to be true and in most cases resistance segregated in an approximate ratio of 3:1 consistent with single locus T-DNA transformants (Table 2). Transgenic progeny resistant to C. fulvum race 5 did not confer resistance to race 4, as predicted since this race does not express the AVR4 peptide (Joosten et al., 1994). This demonstrates that the resistance is a consequence of AVR4 peptide recognition.

Homologue III is completely absent from cosmid 4/5-108 and only truncated copies of this gene are present on the other two cosmids. Therefore Homologue III is an unlikely candidate for Cf-4. It is possible that more than one gene at this locus confers recognition of the AVR4 peptide and pathogen resistance, as occurs in the case of Cf-2 (Dixon et al., 1996). In this latter example however, the two genes are almost identical in contrast to the deduced amino acid sequences of the 3 Cf-9 homologous genes described here. A complete copy of homologue I is present in all 3 cosmids (FIG. 3). Physical mapping and PCR analysis of cosmid 4/5-108 has shown that Homologue II is truncated in this clone lacking 54 amino acids from its C-terminus as well as the 3' untranslated region and associated transcription termination and polyadenylation sequences.

These data clearly implicate homologue II as the Cf-4 gene. PVX:SPAvr4 dependent leaf necrosis and resistance to C. fulvum race 5 is only apparent in transgenic plants transformed with binary vectors containing complete copies of Homologue II (Table 1). Southern hybridization analysis of a number of resistant primary transformants (4/5-129A, 4/5-129B, 4/5-129D, 4/5-129G, 4/5-129H, 4/5-138A and 4/5-138B) with the pCf9XS probe showed they all contained the 3.2 kbp BglII DNA fragment characteristic of Homologue II.

That Homologue II specifically recognizes AVR4 is further substantiated by the results of analysis of transgenic N. tabacum plant containing these 3 cosmids. When inoculated with PVX:SPAvr4 (Table 3), most transformants containing cosmid 4/5-129 (7/10) and cosmid 4/5-138 (4/5) exhibited necrotic lesions at the site of virus inoculation 3–4 d.p.i. similar in appearance to lesions which appear in response to virus inoculation in some virus resistant varieties. In these individuals the necrosis is not strictly confined to local lesions which eventually coalesce and at 7–10 d.p.i. leaf necrosis is apparent over the entire region of virus inoculation. In several transformants the reaction to PVX:SPavr4 is more acute and the necrotic leaf sectors can be observed at 3–4 d.p.i. (Table 3). Neither of these phenotypes were observed in transgenic tobacco containing cosmid 4/5-108 (0/5, see Table 3) or in non-transformed control plants challenged with PVX:SPAVr4.

(6) Analysis of the Protein Encoded by Homologue II.

The DNA sequence of homologue II (SEQ ID NO. 1, hereafter referred to as Cf-4) is shown in FIG. 5. This sequence contains a long uninterrupted open reading frame which upon conceptual translation encodes an 806 amino acid protein as shown in SEQ ID No. 2 (FIG. 6). Nucleic acid sequence homology between Cf-4 and Cf-9 in the 3' flanking regions is extremely high and they are identical between the termination codons and the site of polyadenylation of the Cf-9 transcript as determined by cDNA analysis (Jones et al., 1994).

Analysis of PCR amplified cDNA clones derived from transcripts of Cf-4 show that it also contains an intron in the 3' untranslated region as in Cf-9 (FIG. 5).

Comparison of the Cf-4 amino acid sequence with the 863 amino acid sequence of Cf-9 has shown they are highly homologous (91.5% identity, 95.5% similarity). As in Cf-9, the Cf-4 amino acid sequence has seven predicted structural domains (FIG. 7) as proposed by Jones et al., (1994).

Domain A (amino acids 1–23) is consistent with a signal peptide sequence.

Domain B (amino acids 24–81) corresponds to the mature N-terminus of Cf-4; this region contains a 10 amino acid deletion relative to Cf-9 (FIG. 8).

Domain C (amino acids 82–702) contains 26 imperfect copies of a 24 amino acid LRR sequence. This region contains a 46 amino acid deletion relative to Cf-9 corresponding to 2 complete LRRs beginning in LRR 10 of Cf-9 and finishing in LRR 12 (FIG. 7). Most of the amino acid variation between Cf-9 and Cf-4 is also located in the N-terminal half of the protein (FIG. 7). This probably represents the region in each protein which interacts specifically with the cognate avirulence peptides or with other factors which bind the appropriate avirulence peptides.

In the sequences C-terminal to this region the predicted Cf-4 and Cf-9 proteins are highly homologous; amino acids 455–806 of Cf-4 and 512–863 of Cf-9 (Jones et al., 1994) are identical.

Domain D (amino acids 703–730) has no conspicuous features.

Domain E (amino acids 731–748) is markedly acidic containing 10 negatively charged residues.

Domain F (amino acids 749–785) is very hydrophobic and is consistent with a transmembrane domain.

Domain G (amino acids 786–806) is markedly basic with 8 positively charged residues and only 2 negatively charged residues.

The Cf-4 protein, as with Cf-9, has many of the features predicted for a cell-membrane anchored extracytoplasmic protein.

(7) Tomato Transgenics which Express AVR4 Peptide.

Previous studies have shown that progeny of Cf-9 containing plants crossed to transgenics expressing AVR9 (Hammond-Kosack et al., 1994) exhibit developmentally regulated plant death. Germinating seedlings are phenotypically indistinguishable from their wild type counterparts until 10 days post germination (dpg) when necrosis is observed on cotyledons. The necrosis is progressive and and at is dpg the seedlings die.

We cloned the SP:AVR4 cassette (FIG. 4) into the vector SLJ4K1 (Jones et al., 1992) as a ClaI/BamHI fragment to provide plant promoter (CaMV 35S) and transcription termination (nos3') control sequences for stable expression. This clone was named pAVR4/4K1. The 35S:Avr4 nos3' cassette was excised as a BglII/HindIII fragment and cloned into the binary transformation vector SLJ7291 (FIG. 9) digested with BanHI and HindIII to generate the plasmid pAVR4/7291.

Transgenic plants were generated and screened for AVR4 expression by test crossing to the line Cf4. Test cross progeny were screened for the seedling lethal phenotype. Progeny from crosses with six independent transformants were identified which segregated 1:1 for wild type and necrotic seedlings (AVR4/7291J, AVR4/7291O, AVR4/7291L, AVR4/7291N, AVR4/7291M and AVR4/7291G).

In these progeny the developmental pattern of necrosis was essentially similar to that described in plants expressing AVR9 and Cf-9.

In progeny of another cross between AVR4/7291G (female parent) and a primary transformant expressing Cf-4 (4/5-129H) seedling lethality was observed in 25% of progeny (35 wild type:10 necrotic) as predicted for an intercross between single locus hemizygous plants. These seedlings were germinated in nutrient agar in a growth room and the pattern of necrosis was different from the control crosses described above. Seedlings which eventually exhibited necrosis were stunted relative to their wild type siblings and necrosis was apparent at an earlier developmental stage. Furthermore necrotic sectors were also observed in roots, a phenotype not observed in plants expressing Cf-9 and AVR9. In experiments where progeny of 4/5-129H were inoculated with PVX:SPAvr4, necrosis was apparent earlier than in Cf4 control plants. This phenomenon may reflect elevated Cf-4 expression in transformant 4/5-129H as a consequence of the chromosomal location of T-DNA insertion.

This result suggests that if sufficient levels of Cf-4 can be expressed in non-photosynthetic tissue, such as roots, necrosis can be induced in the presence of AVR4. This result therefore has implications for the use of two-component systems to engineer disease resistance, e.g. WO95/31564, in different tissues in a wide range of plants, such as crop plants, and in particular for engineering resistance to root pathogens such as root colonising fungi or nematodes.

(8) Tomato Transgenics Containing only Homologue II.

To further test the conclusion that Homologue II is responsible for AVR4 recognition and resistance to C. fulvum race 5, tomato transgenics were generated with Homologue II under control of its own promoter or a promoter capable of directing high level gene expression in plants, i.e. the cauliflower mosaic virus 35S promoter (35S, see Jones et al., 1992). These constructions involved DNA manipulations and modifications well known to those skilled in the art.

The 6.0 kbp PstI fragment from cosmid 4/5-129 (129P1, see FIG. 3) was cloned into a modified pUC119 vector lacking EcoRI and HindIII restriction sites from the polylinker sequence to generate clone p129P6A. Oligonucleotide mutagenesis was first performed on this clone to remove internal XbaI and EcoRI restriction sites commencing at nucleotides 308 and 312 respectively (FIG. 5) to generate clone p129P6A-3. These alterations did not alter the predicted amino acid composition of the Cf-4 protein.

To express Homologue II under its own promoter the 6.0 kbp XbaI/BamHI cassette from p129P6A-3 was excised and cloned into XbaI/BamHI digested SLJ7291 (FIG. 9) to generate clone pCf4XB/7291. Further manipulations to p129P6A-3 were performed by oligonucleotide mutagenesis for construction of a vector which might give high level Cf-4 expression in plants. Again, none of the modifications alter the predicted amino acid composition of the Cf-4 protein and all modifications were verified by DNA sequence analysis of the completed construct.

These alterations included the following additional modifications: (i) introduction of a ClaI restriction site (ATCGAT) commencing at nucleotide 197 (FIG. 5) to facilitate fusion to the 35S promoter in construct SLJ4K1 (Jones et al., 1992); (ii) elimination of an internal HindIII restriction site commencing at nucleotide 1766; (iii) elimination of an internal BglII site commencing at nucleotide 2096; (iv) elimination of a ClaI restriction site in the 3' untranslated region commencing at nucleotide 2685.

The modified Homologue II coding sequence and 3' untranslated region was excised as a ClaI/BamHI fragment and cloned into SLJ4K1 (Jones et al., 1992) to produce the plasmid p4K1/Cf4. The 35S:Cf-4 cassette was excised as a BglII/HindIII fragment and cloned into BamHI/HindIII cut SLJ7291 to generate plasmid p35SCf4/7291. Tomato transgenics were generated with both binary vector clones and tested by inoculation with PVX:SPAvr4 or C. fulvum race 5 as described above.

Several independent transformants containing pCf4XB/7291 exhibited systemic necrosis when inoculated with PVX:SPAvr4 (Table 4). Two out of three transgenics tested were also fully resistant to C. fulvum race 5. Eight transgenics containing p35SCf4/7291 exhibited PVX:SPAvr4 dependent necrosis and several tested plants also appeared to give full resistance to C. fulvum race 5 (Table 4).

These results demonstrate that Homologue II is necessary and sufficient for AVR4 recognition and to confer full resistance to C. fulvum race 5.

(9) Tobacco Transgenics Containing only Homologue II.

Previous experiments have shown that the seedling lethal phenotype observed in tomato progeny expressing Cf-9 and AVR9 can also be observed in tobacco. Binary vector plasmids were constructed containing either of two PstI fragments subcloned from cosmid 4/5-129 (FIG. 3). These fragments were cloned into the plasmid SLJ755A using techniques well known to those skilled in the art to generate plasmids p129P1/755 and p129P2/755. The binary vector SLJ755A contains the Streptomyces hygroscopicus BAR gene under control of the A. tumefaciens nos gene promoter (FIG. 9). This gene is used as a transformation marker in plants by conferring resistance to the herbicide phosphinotricin (Jones et al., 1992).

These constructs were used successfully in tobacco transformation experiments but not tomato; for tomato transformation alternative vectors were used (see above).

Transgenic tobacco plants were tested for Cf-4 activity by inoculation with PVX:SPAvr4 to monitor the appearance of necrotic lesions or sectors as observed in the binary cosmid vector transformation experiments described above. None of the seven transgenics containing p129P2/755A showed characteristic necrotic lesions or sectors in contrast to ten out of thirteen transgenics containing p129P1/755A (Table 5).

This result is again consistent with the previous observations that Homologue II confers Cf-4 function.

Tobacco transgenics containing pAVR4/7291 (see above) were also generated. Primary transformants containing p129P1/755A expressing Cf-4 were crossed (as female parents) to pAVR4/7291 transgenics to identify AVR4 expressing individuals by monitoring seedling lethality in F1 progeny. Several transgenics expressing AVR4 were identified (AVR4/7291 I, AVR4/7291 K and AVR4/7291 J).

In $F_1$ progeny of all crosses tested (Table 5) lethality was observed in 25% of seedlings as predicted for progeny of single T-DNA locus hemizygous parents if both transgenics are required for lethality. No variation in the developmental expression of seedling lethality was observed, at least at the macroscopic level, in progeny of the various crosses. However, the phenotyype observed in the Cf-4/AVR4 interaction is distinct from the phenotype observed in the Cf-9/AVR9 interaction.

Specifically, tobacco seedling lethality is observed at an earlier stage in seedling development. At seven days post-sowing (on nutrient agar) wild type siblings can be readily distinguished from those expressing Cf-4/AVR4. Cotyledons of seedlings expressing Cf-4 and AVR4 do not expand completely and do not produce appreciable quantities of chlorophyll. In the majority of seedlings the testa remains either attached to one cotyledon or enclosing both.cotyledons. This latter feature was not observed in Cf-9/AVR9 expressing tobacco seedlings. At fourteen days post-sowing cotyledons of seedlings expressing Cf-4 and AVR4 appear completely necrotic. These seedlings also fail to develop extensive root systems as reported for the Cf-9/AVR9 interaction.

These results suggest that seedling lethality is expressed at an earlier developmental stage than that described for the Cf-9/AVR9 interaction.

(10) Transient Expression Assays to Monitor Cf-4 and Cf-9 Activity

Experiments in our laboratory have shown that genes on a binary vector plasmid under control of the CaMV 35S promoter can be transiently expressed in Nicotiana tabacum leaf cells when delivered into leaves by infiltrating suspensions of A. tumefaciens bacteria. In experiments with 35S:Cf-9 infiltrated leaf panels of stable transgenics expressing AVR9, necrosis was observed in the infiltrated areas. The phenotype was specific to plants expressing AVR9. Other experiments with intron-containing versions of the uida (GUS) reporter gene demonstrated this phenomenon is a consequence of plant nuclear gene expression. The procedure we have used in tobacco was modified from a protocol developed to assay transient gene expression in leaves of Phaseolus vulgaris.

Binary vector plasmids were mobilized into A. tumefaciens GV3101/pMP90 by tri-parental mating, a technique well known to those skilled in the art. Single colonies grown on L broth medium containing the antibiotics rifampicin (50 $\mu$ml) and tetracycline (1 $\mu$g/ml) were picked and grown in 5 ml L-broth containing antibiotics for 48 h at 28° C. in a shaking incubator. One ml of this saturated culture was inoculated into 100 ml L-broth containing antibiotics, 10 mM(2-[N-Morpholino]ethane sulfonic acid (MES) pH. 5.6 and 20 $\mu$M acetosyringone to induce Agrobacterium Vir gene. Cultures were grown for 16 h at 28° C. in a shaking incubator. Bacterial cells were pelleted by low speed centrifugation and resuspended in a buffer containing Murashige and Skoog (MS) salts, 2% w/v sucrose, 500 $\mu$M MES pH 5.6 and 10 $\mu$M acetosyringone. The $OD_{600}$ of each culture was determined and adjusted to an $OD_{600}$ of 0.5. Cultures were then incubated without shaking for 3 h at 22° C.

Mature leaves of N. tabacum were infiltrated with Agrobacterium suspensions using a syringe after several small incisions had been made in the target leaf panel. After injection of several panels infiltrated leaves were covered in a plastic bag to prevent desiccation. After 72 h the bag was removed.

Similar experiments were performed using Agrobacterium containing a 35S:Cf-4 binary vector, infiltrated into leaves of N. tabacum constitutively expressing AVR4 (see section above). A binary vector containing 35S:Cf-4 was constructed as follows.

The 1.8 kbp ClaI/BamHI fragment encoding the uida (GUS) gene from E. coli was replaced in binary vector SLJ10080 with the 2.9 kbp ClaI/BamHI fragment encoding Cf-4 derived from plasmid p4K1/CF4 (see Section 8). Similar modifications involving oligonucleotide mutageneis of Cf-9 DNA were performed as described above to generate a similar construct. The resulting binary vector plasmids pCf4/10080 and pCf9/10080 were mobilized into A. tumefaciens.

In transient expression assays Agrobacterium suspensions containing pCf4/10080 and pCf9/10080 or a control containing no binary vector, all induced no visible necrosis on non-transformed tobacco. Only leaf panels infiltrated with pCf9/10080 induced a necrotic response on AVR9 expressing tobacco 5–6 days post-infiltration. In the transgenic plant AVR4/7291 K (see Section 9) only leaf panels injected with pCf4/10080 induced a visible necrosis 5–6 days post-infiltration.

This assay therefore, provides a quick and reliable procedure to test both Cf-9 and Cf-4 gene function in other species, and the effect of specific mutations without the need to generate stable transgenic plants expressing the modified Cf genes.

We also reasoned that in transient assays, vectors carrying both the 35S:Cf-4 or 35S:Cf-9 gene construct and the corresponding 35S:Avr gene construct, may result in a visible necrosis in infiltrated leaves. If so, the assay may provide a method to determine the range of species in which Cf-4 and Cf-9 can function but without the need to generate transgenic plants expressing either the resistance gene or avirulence gene component. This could have important implications in utilization of a Cf-gene/avirulence gene two-component system to engineer resistance in other crop species WO95/31564.

Binary vector plasmids containing both the resistance gene and the avirulence gene were constructed as follows. The 35S:Cf-4 and 35S:Cf-9 cassettes were excised from pCf4/10080 and pCf9/10080 as follows: (i) digestion with ApaI and T4 DNA polymerase treatment to blunt end the DNA fragments; (ii) digestion with PstI to release the 35S:Cf-4 and 35S:Cf-9 cassettes; (iii) the vector SLJ456 (Jones et al., 1992) was linearized with ClaI and treated with T4 DNA polymerase to blunt end the DNA and subsequently digested with PstI to release the 2.1 kbp neomycin phosphotransferase (NPT) reporter gene fragment; (iv) the 4.3 kbp 35S:Cf-4 and 4.5 kbp 35S:Cf-9 ApaI(T4)/PstI fragments were cloned into ClaI(T4)/PstI treated SLJ456 to generate plasmids p4/456 and p9/456. All these techniques are well known to those skilled in the art.

Avirulence gene constructs were made as follows.

The clone pAVR4/4K1 (see Section 9) was digested with EcoRI and BamHI to excise the 35S:AVR4 cassette. The purified fragment was ligated to the approximately 3.9 kbp EcoRI/BamHI fragment from SLJ6B1 (Jones et al., 1992) to generate the plasmid pAVR4/6B1 containing 35S, AVR4 and the transcription terminator of the A. tumefaciens octopine synthase gene (ocs3') A 35S:Avr0:ocs3' construct was made in a similar way from the clone SLJ6071 (Hammond-Kosack et al., 1994) to generate plasmid pAVR9/6B1. The plasmids pAVR4/6B1 and pAVR9/6B1 were linearized with HindIII and treated with T4 DNA polymerase to blunt end the DNA fragment. The 35S:AVR4:ocs3' and 35S:AVR9:ocs' cassettes were released by treatment with BglII. The purified cassettes were each ligated to BamHI/HpaI treated p4/456 and p9/456 to generate four different plasmids in which the function of each resistance gene (Cf-4 or Cf-9)could be assayed in combination with either AVR4 or AVR9.

Four leaf panels on single leaves of Nicotania benthamiana plants were infiltrated with Agrobacterium containing each of the four plasmids shown in FIG. 11. Leaf necrosis was observed five days post-infiltration in panels which received the vector p4/456/Avr4. No necrosis was observed in panels injected with p4/456/Avr9 showing the latter result is a consequence of co-expression of Cf-4 and AVR4 in the is same cells.

After seven days the necrotic leaves were detached and stored in a sealed polythene bag at room temperature. Necrosis was eventually observed in the leaf panel injected with p9/456/Avr9 but not p9/456/Avr4 twelve days post-infiltration.

These experiments demonstrate that Cf-gene necrosis inducing activity can be detected in a transient expression assay in other species when the cognate avirulence determinant is co-expressed. Necrosis induced by the Cf-4/AVR4 interaction appeared significantly earlier than that induced by the Cf-9/AVR9 interaction. Since all promoter, translation and termination control sequences are the same in each construct, the latter phenomenon might reflect differences in the relative affinity of Cf-4 and Cf-9 for their corresponding avirulence gene products. This theory would be consistent with the earlier appearance of the seedling lethal phenotype in tobacco transgenics expressing Cf-4 and AVR4 compared to those expressing Cf-9 and AVR9.

TABLE 1

Phenotypes observed in transgenic tomato plants containing cosmids 4/5-108, 4/5-129, or 4/5-138. Plants exhibiting necrotic lesions on inoculated leaves in response to PVX:SPAvr4, which eventually spread systemically are denoted by a (+) sign; plants showing no visible symptoms are denoted by a (−) sign. Plants were also assayed for Cf-4 function by inoculation with C. fulvum race 5; R = resistant, S = sensitive.

| Transformant | Response to PVX:SPAvr4 | Pathogen inoculation. |
|---|---|---|
| 4/5-108A | − | S |
| 4/5-108B | − | S |
| 4/5-108C | − | S |
| 4/5-129A | + | R |
| 4/5-129B | + | R |
| 4/5-129C | − | S |
| 4/5-129D | + | R |
| 4/5-129E | + | R |
| 4/5-129F | − | S |
| 4/5-129G | + | R |
| 4/5-129H | + | R |
| 4/5-138A | + | R |
| 4/5-138B | + | R |
| 4/5-138C | − | S |
| 4/5-138D | + | R |

TABLE 2 pathogen inoculation tests on Cf control lines (Cf0, Cf4 and Cf5) and progeny of several primary transformants. Plants were inoculated either with C. fulvum race 5 or race 4. Progeny of resistant primary transformants which were previously shown to be resistant to C. fulvum race 5 but susceptible to infection by race 4. In most cases progeny segregated at an approximate ratio of 3:1 resistant:susceptible.

| Tomato genotype | C. fulvum (race 5). | | C. fulvum (race 4). | |
|---|---|---|---|---|
|  | S | R | S | R |
| Cf4 | 0 | 20 | 15 | 0 |
| Cf0 | 20 | 0 | 15 | 0 |
| Cf5 | 19 | 0 | 0 | 20 |
| 4/5-108B | 42 | 0 | 18 | 0 |
| 4/5-129B | 11 | 23 | 15 | 0 |
| 4/S-129C | 39 | 0 | 18 | 0 |
| 4/S-129D | 13 | 29 | 19 | 0 |
| 4/5-129H | 15 | 20 | 18 | 0 |
| 4/S-138B | 10 | 28 | 20 | 0 |

TABLE 3

Description of phenotypes observed in transgenic tobacco containing cosmids 4/5-108, 4/5-129 or 4/5-138 at 3–4 days post inoculation with PVX:SPAvr4 (for description of phenotypes see text). NVS = no visible symptoms

| Transformant | Symptoms after PVX:SPAvr4 inoculation. |
|---|---|
| 4/5-108A | NVS |
| 4/5-108B | NVS |
| 4/5-108C | NVS |
| 4/5-108D | NVS |
| 4/5-108E | NVS |
| 4/5-129A | Local necrotic lesions |
| 4/5-129B | Local necrotic lesions |
| 4/S-129C | NVS |
| 4/5-129D | NVS |
| 4/5-129E | NVS |
| 4/5-129F | Necrotic leaf sector |
| 4/s-129G | Necrotic leaf sector |
| 4/5-129H | Necrotic leaf sector |
| 4/5-129I | Necrotic leaf sector |
| 4/5-129J | Necrotic leaf sector |
| 4/5-138A | Local necrotic lesions |
| 4/5-138C | Local necrotic lesions + leaf necrosis |
| 4/5-138E | NVS |
| 4/5-138H | Local necrotic lesions |
| 4/5-138J | Local necrotic lesions + leaf necrosis |

TABLE 4

| Transformant | PVX:SPAVR4 | C. fulvum race 5 |
|---|---|---|
| Cf4XB/7291A | + | R |
| Cf4XB/7291B | − | S |
| Cf4XB/7291C | + | ND |
| Cf4XB/7291D | + | R |
| Cf4XB/7291F | + | ND |
| Cf4XB/7291H | − | ND |
| 35SCf4/7291B | + | R |
| 35SCf4/7291C | (ND) | R |
| 35SCf4/7291D | + | R |
| 35SCf4/7291E | + | R |
| 35SCf4/7291F | + | R |
| 35SCf4/7291G | + | R |
| 35SCf4/7291H | + | ND |
| 35SCf4/7291I | ND | R |
| 35SCf4/7291J | + | R |
| 35SCf4/7291K | + | R |
| 35SCf4/7291P | − | S |
| 35SCf4/7291Q | ND | R |

Phenotypes obvserved in transgenic tomato plants containing vectors pCFXB/7291 and p35SCf4/7291. Plants exhibiting necrotic lesions on inoculated leaves in response to PVX:SPAvr4, which eventually spread systemically are denoted by a (+) sign; plants showing no visible symptoms are denoted by a (−) sign. Plants were also assayed for Cf-4 function by inoculation with C. fulvum race 5; R = resistant, S = sensitive   ND = not determined.

TABLE 5

Expression of Homologue II from its own promoter in transgenic tobacco. Transgenics were assayed for Cf-4 activity by inoculation with PVX:SPAVR4. Plants exhibiting necrotic lesions or sectors are indicated by a (+) and those exhibiting no response by (−). Only transgenics containing Homologue II (129P1/755) conferred Cf-4 function. Several Cf-4 expressing plants were subsequently crossed to different transgenics (AVR4/7291 I, J or K) expressing AVR4 as indicated in the Table. Seedlings of all these crosses segregated 3:1 for either a wild type or necrotic phenotype.

| Transgenic | PVX:SPAVR4 | Seedling lethality |
|---|---|---|
| 129P1/755 A | + | AVR4/7291 J |
| 129P1/755 B | + | ND |
| 129P1/755 C | − | ND |
| 129P1/755 D | + | AVR4/7291 K |
| 129P1/7S5 E | + | AVR4/7291 J and K |
| 129P1/755 F | + | AVR4/7291 J and K |
| 129P1/755 G | + | ND |
| 129P1/755 H | + | ND |
| 129P1/755 I | + | AVR4/7291 I |
| 129P1/755 J | + | ND |
| 129P1/755 L | − | ND |
| 129P1/755 N | ND | AVR4/7291 K, and I |
| 129P1/755 O | + | ND |
| 129P2/755 A | − | ND |
| 129P2/755 B | − | ND |
| 129P2/755 D | − | ND |
| 129P2/755 E | − | ND |
| 129P2/755 G | − | ND |
| 129P2/755 J | − | ND |
| 129P2/755 K | − | ND |

REFERENCES

Ashfield T, et al., (1994) Mol.Plant.Mic.Int. 7:645–657.

Balint-Kurti P, et al., Theor.App.Genet. (1994) 88:691–700.

Bent, A. F., et al., (1994) Science 265:1856–1860

Bevan, M. (1984) Nucl. Acids. Res, 12:8711–8721

Birnboim, H. C. and Doly, J. (1979) Nucl. Acids. Res. 7:1513–1520.

De Wit, PJGM (1992) Ann.Rev.Phytopathol. 30:391–418.

Dickinson M, et al., (1993) Mol.Plant Mic.Int. 6:341–347.

Dixon, et al., (1996) Cell. 84:451–459.

Fillatti J J, et al. (1987). Bio/technol. 5:726–730.

Flor H H (1971). Ann.Rev.Phytopathol. 9:275–296.

Gabriel D W, et al. (1990). Ann. Rev. Phytopathol. 28:365–391.

Grant, et al. (1995). Science 269:843–846.

Hammond-Kosack KE, et al. (1994) Mol. Plant.Mic.Int. 7:58–70.

Hammond-Kosack, et al., (1994) PNAS (USA) 91:10445–10449.

Hammond-Kosack et al. (1995) Mol. Plant-Microbe Interact. 8:181–185

Horsch R B, et al. (1985). Science (Wash.). 227:1229–1231.

Jones D A, et al. (1993). Mol.Plant Mic.Int. 6:348–357.

Jones D A, et al. (1994). Science (Wash.) 266:789–793.

Jones, et al., (1992). Transgenic Research 1:285–297.

Joosten et al. (1994) Nature 367:384–367.

Lawrence, et al., (1995). Cell 7:1195–1206.

Martin G B, et al., (1993). Science 262:1432–1436.

Mindrinos M, et al., (1994). Cell 78:1089–1055.

Sambrook, et al., (1989). Molecular Cloning: A Laboratory Manual (NY: Cold Spring Harbor).

Song, et al., (1995). Science 270:1804–1806.

Staskawicz et al. (1995) Science 268:661–667

Tanskley et al. (1995) Trends Genet. 11:63–68

Thomas et al (1994) Mol. Gen. Genet. 242:573–585

Thomas et al (1995) "Identification of amplified restriction fragment polymorphism (AFLP) markers tightly lined to the tomato Cf-9 gene for resistance to *Cladosporium fulvum*" (Submitted to The Plant Journal) van Kan et al. (1991) Mo. Plant-Microbe Interact. 4:52–59

Fritjers, et al., (1995). Nucl. Acids Res. 23:4407–4414.

Whitham S, et al. (1994). Cell 78:1011–1115.

Williams et al (1990) Nucl. Acids Res. 18:6531–6535.

What is claimed is:

1. An isolated nucleic acid the expression of which in a plant causes activation of a defense response in the plant upon contact of the plant with a pathogen expressing Avr4 elicitor molecule or upon contact of the plant with Avr4 elicitor molecule, the nucleic acid comprising a sequence of nucleotides encoding a polypeptide comprising the sequence of amino acids shown in SEQ ID NO:2.

2. The nucleic acid according to claim 1 wherein the sequence of nucleotides comprises the encoding sequence shown in SEQ ID NO:1.

3. An isolated nucleic acid the expression of which in a plant causes activation of a defense response in the plant upon contact of the plant with a pathogen expressing Avr4 elicitor molecule or upon contact of the plant with Avr4 elicitor molecule, the nucleic acid comprising a sequence of nucleotides encoding a polypeptide, the polypeptide having an amino acid sequence which has at least 95% amino acid sequence identity with the amino acid sequence shown in SEQ ID NO:2.

4. A vector comprising said nucleic acid according to claim 1 or claim 3.

5. The vector according to claim 4 further comprising regulatory sequences for expression of said polypeptide operably linked to said nucleic acid.

6. A host cell comprising the nucleic acid according to claim 1 or claim 3.

7. The host cell according to claim 6 which is microbial.

8. The host cell according to claim 6 which is a plant cell.

9. A plant or any part thereof comprising the cell according to claim 8.

10. A seed, selfed or hybrid progeny or a descendant or derivative or extract of a plant according to claim 9.

11. A method of producing a transformed host cell which comprises introducing the nucleic acid according to claim 1 or claim 3 into a host cell so that said transformed host cell is produced.

12. The method according to claim 11 wherein the host cell is a plant or microbial cell.

13. A method of conferring pathogen resistance on a plant, comprising introducing the nucleic acid according to claim 1 or claim 3 into cells of said plant and effecting expression of said nucleic acid whereby said pathogen resistance is conferred on said plant.

14. The method according to claim 13 wherein the nucleic acid encodes the amino acid sequence shown in SEQ ID NO:2.

15. An isolated nucleic acid encoding the amino acid sequence shown in SEQ ID NO:2.

16. The nucleic acid according to claim 15 which comprises the encoding sequence shown in SEQ ID NO:1.

17. The nucleic acid according to claim 15 further comprising regulatory sequences for expression of said polypeptide operably linked to said nucleic acid.

18. A host cell comprising the nucleic acid according to claim 15.

19. A plant or any part thereof comprising the cell according to claim 18, wherein said cell is a plant cell.

20. A method of producing a transformed host cell which comprises introducing the nucleic acid according to claim 15 into a host cell so that said transformed host cell is produced.

21. A method of conferring pathogen resistance on a plant, comprising introducing the nucleic acid according to claim 15 into cells of said plant and effecting expression of said nucleic acid whereby said pathogen resistance is conferred on said plant.

* * * * *

UNITED STATES PATENT AND TRADEMARK OFFICE
CERTIFICATE OF CORRECTION

PATENT NO.    : 6,225,527 B1                                                   Page 1 of 1
DATED         : May 1, 2001
INVENTOR(S)   : Thomas et al.

It is certified that error appears in the above-identified patent and that said Letters Patent is hereby corrected as shown below:

<u>Title page,</u>
Item [30], change
"[30]   Foreign Application Priority Data
  Nov. 5, 1995         (GB) ................................. 9509575" to read as:
-- [30]   Foreign Application Priority Data
  May 11, 1995         (GB) ................................. 9509575 --

Signed and Sealed this

Twenty-fifth Day of November, 2003

JAMES E. ROGAN
*Director of the United States Patent and Trademark Office*

SEQUENCE LISTING

```
(1) GENERAL INFORMATION:

(iii) NUMBER OF SEQUENCES: 9

(2) INFORMATION FOR SEQ ID NO:1:

(i) SEQUENCE CHARACTERISTICS:
          (A) LENGTH: 3090 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (vi) ORIGINAL SOURCE:
          (A) ORGANISM: Lycopersicon hirsutum
          (B) STRAIN: Cf4

(xi) SEQUENCE DESCRIPTION: SEQ ID NO:1:

GACCAAACTG GACTCCTGCT CCGTCTTCCA TCAGCAGGTC AATTCTCGTG GAAAATTAGC      60

TCGAGGTGGC GCACTATGTG AGGTAGCTAG TACTAAATGT TTATTTGCGT AATTTGTGCT     120
```

```
ATATATACCT CATCTAAATT ATTGAATAGA CACACAAAGC AAACATCTCT TAATTAGTTT       180

TGATCATTTT TAGTGCAGAA ATGGGTTGTG TAAAACTTGT GTTTTTCATG CTATATGTCT       240

TTCTCTTTCA ACTTGTTTCC TCGTCATCCT TACCTCATTT GTGCCCCGAA GATCAAGCTC       300

TTGCTCTTCT AGAATTCAAG AACATGTTTA CCGTTAATCC TAATGCTTCT GATTATTGTT       360

ACGACAGAAG AACTCTTTCT TGGAACAAAA GCACAAGTTG CTGCTCATGG GATGGCGTTC       420

ATTGTGACGA AACGACAGGA CAAGTGATTG AGCTTGACCT CCGTTGCATC CAACTTCAAG       480

GCAAGTTTCA TTCCAATAGT AGCCTCTTTC AACTCTCCAA TCTCAAAAGG CTTGATTTGT       540

CTTATAATGA TTTCACTGGA TCGCCCATTT CACCTAAATT TGGTGAGTTT TCAGATTTGA       600

CGCATCTCGA TTTGTCGCAT TCAAGTTTTA GGGGTGTAAT CCCTTCTGAA ATCTCTCATC       660

TTTCTAAACT ATACGTTCTT CGTATTAGTC TAAATGAGCT TACTTTTGGT CCTCACAATT       720

TTGAATTGCT TCTTAAGAAC TTGACCCAAT TAAAAGTGCT CGACCTTGAA TCTATCAACA       780

TCTCTTCCAC TATTCCTTTG AATTTCTCTT CTCATTTAAC AAATCTATGG CTTCCATACA       840

CAGAGTTACG TGGGATATTG CCCGAAAGAG TTTTCCACCT TTCCGACTTA GAATTTCTCG       900

ATTTATCAAG CAATCCCCAG CTCACGGTTA GGTTTCCCAC AACCAAATGG AATAGCAGTG       960

CATCACTCAT GAAGTTATAT CTCTATAATG TGAATATTGA TGATAGGATA CCTGAATCAT      1020

TTAGCCATCT AACTTCACTT CATAAGTTGT ACATGAGTCG TTCTAATCTG TCAGGGCCTA      1080

TTCCTAAACC TCTATGGAAT CTCACCAACA TAGTGTTTTT GGACCTTAAT AATAACCATC      1140

TTGAAGGACC AATTCCATCC AACGTAAGCG GACTACGTAA CCTACAAATA CTTTGGTTGT      1200

CATCAAACAA CTTAAATGGG AGTATACCAT CCTGGATATT CTCCCTTCCA TCACTGATAG      1260

GGTTAGACTT GAGCAATAAC ACTTTCAGTG GAAAAATTCA AGAGTTCAAG TCCAAAACAT      1320

TAAGTACCGT TACTCTAAAA CAAAATAAGC TAAAAGGTCC TATTCCGAAT TCACTCCTAA      1380

ACCAGAAGAA CCTACAATTC CTTCTCCTTT CACACAATAA TATCAGTGGA CATATTTCTT      1440

CAGCTATCTG CAATCTGAAA ACATTGATAT TGTTAGACTT GGGAAGTAAT AATTTGGAGG      1500

GAACAATCCC GCAATGCGTG GTTGAGAGGA ACGAATACCT TTCGCATTTG GATTTGAGCA      1560

ACAACAGACT TAGTGGGACA ATCAATACAA CTTTTAGTGT TGGAAACATT TTAAGGGTCA      1620

TTAGCTTGCA CGGGAATAAG CTAACGGGGA AAGTCCCACG ATCTATGATC AATTGCAAGT      1680

ATTTGACACT ACTTGATCTA GGTAACAATA TGTTGAATGA CACATTTCCA AACTGGTTGG      1740

GATACCTATT TCAATTGAAG ATTTTAAGCT TGAGATCAAA TAAGTTGCAT GGTCCCATCA      1800

AATCTTCAGG GAATACAAAC TTGTTTATGG GTCTTCAAAT TCTTGATCTA TCATCTAATG      1860

GATTTAGTGG GAATTTACCC GAAAGAATTT TGGGGAATTT GCAAACCATG AAGGAAATTG      1920

ATGAGAGTAC AGGATTCCCA GAGTATATTT CTGATCCATA TGATATTTAT TACAATTATT      1980

TGACGACAAT TTCTACAAAG GGACAAGATT ATGATTCTGT TCGAATTTTG GATTCTAACA      2040

TGATTATCAA TCTCTCAAAG AACAGATTTG AAGGTCATAT TCCAAGCATT ATTGGAGATC      2100

TTGTTGGACT TCGTACGTTG AACTTGTCTC ACAATGTCTT GGAAGGTCAT ATACCGGCAT      2160

CATTTCAAAA TTTATCAGTA CTCGAATCAT GGATCTCTC ATCTAATAAA ATCAGCGGAG      2220

AAATTCCGCA GCAGCTTGCA TCCCTCACAT TCCTTGAAGT CTTAAATCTC TCTCACAATC      2280

ATCTTGTTGG ATGCATCCCC AAAGGAAAAC AATTTGATTC GTTCGGGAAC ACTTCGTACC      2340

AAGGGAATGA TGGGTTACGC GGATTTCCAC TCTCAAAACT TTGTGGTGGT GAAGATCAAG      2400

TGACAACTCC AGCTGAGCTA GATCAAGAAG AGGAGGAAGA AGATTCACCA ATGATCAGTT      2460

GGCAGGGGGT TCTCGTGGGT TACGGTTGTG GACTTGTTAT TGGACTGTCC GTAATATACA      2520
```

-continued

```
TAATGTGGTC AACTCAATAT CCAGCATGGT TTTCGAGGAT GGATTTAAAG TTGGAACACA    2580

TAATTACTAC GAAAATGAAA AAGCACAAGA AAAGATATTA GTGAGTAGCT ATACCTCCAG    2640

GTATTCCACT TGATCATTAT CTTTCAGAAG ATTATTTTTT GTATATCGAT GAAATTATCG    2700

ACCTCCTTCA TCCTCAAAGC TCTTAACTTT CACTCTTCAT TTTTGAAAAT TTCAGGATTC    2760

AAAGATTTCC GAGTTCCCAG TTGCTTGGGA TGCAGATAAA AGCCTTTTTA TCTTTCATAG    2820

TTTCTTATCC TATGAATAAA GATTTTATTT TCATTTGTCT ATGGCACGTA GATATGTTCC    2880

GTCACTAAAA ACATTGTATT TCTCTCAACT CTTTCGTCAC ATGATATCAA AGAACACTTG    2940

ACTTCAATTA AGTTACTGTA GTCTGCTATT TTAATTTCTT CCATTGAAAC ACAACTGACG    3000

TATCTTGAGA AAGAGACTAT GATCTCAGAA ATGGGAATCT CCCAATCCAA AACTCGGAAA    3060

ATCTAGTATC AAACACACCC GACCCTGCAG                                    3090
```

(2) INFORMATION FOR SEQ ID NO:2:

(i) SEQUENCE CHARACTERISTICS:
        (A) LENGTH: 806 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: lycopersicon hirsutum
        (B) STRAIN: Cf4

(xi) SEQUENCE DESCRIPTION: SEQ ID NO:2:

```
Met Gly Cys Val Lys Leu Val Phe Phe Met Leu Tyr Val Phe Leu Phe
 1               5                  10                  15

Gln Leu Val Ser Ser Ser Leu Pro His Leu Cys Pro Glu Asp Gln
            20                  25                  30

Ala Leu Ala Leu Leu Glu Phe Lys Asn Met Phe Thr Val Asn Pro Asn
        35                  40                  45

Ala Ser Asp Tyr Cys Tyr Asp Arg Arg Thr Leu Ser Trp Asn Lys Ser
    50                  55                  60

Thr Ser Cys Cys Ser Trp Asp Gly Val His Cys Asp Glu Thr Thr Gly
65                  70                  75                  80

Gln Val Ile Glu Leu Asp Leu Arg Cys Ile Gln Leu Gln Gly Lys Phe
                85                  90                  95

His Ser Asn Ser Ser Leu Phe Gln Leu Ser Asn Leu Lys Arg Leu Asp
            100                 105                 110

Leu Ser Tyr Asn Asp Phe Thr Gly Ser Pro Ile Ser Pro Lys Phe Gly
        115                 120                 125

Glu Phe Ser Asp Leu Thr His Leu Asp Leu Ser His Ser Ser Phe Arg
    130                 135                 140

Gly Val Ile Pro Ser Glu Ile Ser His Leu Ser Lys Leu Tyr Val Leu
145                 150                 155                 160

Arg Ile Ser Leu Asn Glu Leu Thr Phe Gly Pro His Asn Phe Glu Leu
                165                 170                 175

Leu Leu Lys Asn Leu Thr Gln Leu Lys Val Leu Asp Leu Glu Ser Ile
            180                 185                 190

Asn Ile Ser Ser Thr Ile Pro Leu Asn Phe Ser Ser His Leu Thr Asn
```

-continued

```
            195                 200                 205
Leu Trp Leu Pro Tyr Thr Glu Leu Arg Gly Ile Leu Pro Glu Arg Val
    210                 215                 220

Phe His Leu Ser Asp Leu Glu Phe Leu Asp Leu Ser Ser Asn Pro Gln
225                 230                 235                 240

Leu Thr Val Arg Phe Pro Thr Thr Lys Trp Asn Ser Ser Ala Ser Leu
                245                 250                 255

Met Lys Leu Tyr Leu Tyr Asn Val Asn Ile Asp Asp Arg Ile Pro Glu
            260                 265                 270

Ser Phe Ser His Leu Thr Ser Leu His Lys Leu Tyr Met Ser Arg Ser
        275                 280                 285

Asn Leu Ser Gly Pro Ile Pro Lys Pro Leu Trp Asn Leu Thr Asn Ile
    290                 295                 300

Val Phe Leu Asp Leu Asn Asn His Leu Glu Gly Pro Ile Pro Ser
305                 310                 315                 320

Asn Val Ser Gly Leu Arg Asn Leu Gln Ile Leu Trp Leu Ser Ser Asn
                325                 330                 335

Asn Leu Asn Gly Ser Ile Pro Ser Trp Ile Phe Ser Leu Pro Ser Leu
            340                 345                 350

Ile Gly Leu Asp Leu Ser Asn Asn Thr Phe Ser Gly Lys Ile Gln Glu
        355                 360                 365

Phe Lys Ser Lys Thr Leu Ser Thr Val Thr Leu Lys Gln Asn Lys Leu
    370                 375                 380

Lys Gly Pro Ile Pro Asn Ser Leu Leu Asn Gln Lys Asn Leu Gln Phe
385                 390                 395                 400

Leu Leu Leu Ser His Asn Asn Ile Ser Gly His Ile Ser Ser Ala Ile
                405                 410                 415

Cys Asn Leu Lys Thr Leu Ile Leu Leu Asp Leu Gly Ser Asn Asn Leu
            420                 425                 430

Glu Gly Thr Ile Pro Gln Cys Val Val Glu Arg Asn Glu Tyr Leu Ser
        435                 440                 445

His Leu Asp Leu Ser Asn Asn Arg Leu Ser Gly Thr Ile Asn Thr Thr
    450                 455                 460

Phe Ser Val Gly Asn Ile Leu Arg Val Ile Ser Leu His Gly Asn Lys
465                 470                 475                 480

Leu Thr Gly Lys Val Pro Arg Ser Met Ile Asn Cys Lys Tyr Leu Thr
                485                 490                 495

Leu Leu Asp Leu Gly Asn Asn Met Leu Asn Asp Thr Phe Pro Asn Trp
            500                 505                 510

Leu Gly Tyr Leu Phe Gln Leu Lys Ile Leu Ser Leu Arg Ser Asn Lys
        515                 520                 525

Leu His Gly Pro Ile Lys Ser Ser Gly Asn Thr Asn Leu Phe Met Gly
    530                 535                 540

Leu Gln Ile Leu Asp Leu Ser Ser Asn Gly Phe Ser Gly Asn Leu Pro
545                 550                 555                 560

Glu Arg Ile Leu Gly Asn Leu Gln Thr Met Lys Glu Ile Asp Glu Ser
                565                 570                 575

Thr Gly Phe Pro Glu Tyr Ile Ser Asp Pro Tyr Asp Ile Tyr Tyr Asn
            580                 585                 590

Tyr Leu Thr Thr Ile Ser Thr Lys Gly Gln Asp Tyr Asp Ser Val Arg
        595                 600                 605

Ile Leu Asp Ser Asn Met Ile Ile Asn Leu Ser Lys Asn Arg Phe Glu
    610                 615                 620
```

```
Gly His Ile Pro Ser Ile Ile Gly Asp Leu Val Gly Leu Arg Thr Leu
625                 630                 635                 640

Asn Leu Ser His Asn Val Leu Glu Gly His Ile Pro Ala Ser Phe Gln
            645                 650                 655

Asn Leu Ser Val Leu Glu Ser Leu Asp Leu Ser Ser Asn Lys Ile Ser
            660                 665                 670

Gly Glu Ile Pro Gln Gln Leu Ala Ser Leu Thr Phe Leu Glu Val Leu
            675                 680                 685

Asn Leu Ser His Asn His Leu Val Gly Cys Ile Pro Lys Gly Lys Gln
            690                 695                 700

Phe Asp Ser Phe Gly Asn Thr Ser Tyr Gln Gly Asn Asp Gly Leu Arg
705                 710                 715                 720

Gly Phe Pro Leu Ser Lys Leu Cys Gly Gly Glu Asp Gln Val Thr Thr
                725                 730                 735

Pro Ala Glu Leu Asp Gln Glu Glu Glu Glu Asp Ser Pro Met Ile
            740                 745                 750

Ser Trp Gln Gly Val Leu Val Gly Tyr Gly Cys Gly Leu Val Ile Gly
            755                 760                 765

Leu Ser Val Ile Tyr Ile Met Trp Ser Thr Gln Tyr Pro Ala Trp Phe
770                 775                 780

Ser Arg Met Asp Leu Lys Leu Glu His Ile Ile Thr Thr Lys Met Lys
785                 790                 795                 800

Lys His Lys Lys Arg Tyr
            805

(2) INFORMATION FOR SEQ ID NO:3:

(i) SEQUENCE CHARACTERISTICS:
        (A) LENGTH: 484 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (v) FRAGMENT TYPE: N-terminal (vi) ORIGINAL SOURCE:
        (A) ORGANISM: Nicotiana tabacum/Cladosporium fulvum
        (B) STRAIN: Cladosporium fulvum race 2,5

(vii) IMMEDIATE SOURCE:
        (B) CLONE: SP:AVR4

(xi) SEQUENCE DESCRIPTION: SEQ ID NO:3:

ATCGATGGGA TTTGTTCTCT TTTCACAATT GCCTTCATTT CTTCTTGTCT CTACACTTCT    60

CTTATTCCTA GTAATATCCC ACTCTTGCCG TGCCAAAGCC CCCAAAACTC AACCATACAA   120

CCCATGCAAG CCCCAAGAAG TCATCGACAC CAAGTGTATG GGTCCCAAGG ATTGTCTCTA   180

CCCGAACCCC GACAGTTGTA CAACCTACAT ACAGTGTGTA CCGCTCGACG AAGTTGGCAA   240

TGCGAAGCCT GTGGTTAAGC CATGTCCAAA AGGACTGCAG TGGAACGATA ACGTTGGCAA   300

GAAGTGGTGC GACTATCCAA ACCTGAGTAC GTGTCCGGTA AAGACGCCGC AACCGAAGCC   360

GAAGAAGGGA GGTGTCGGAG GGAAGAAGGC GTCGGTTGGA CATCCTGGCT ATTGAGTCGG   420

ACAAGAAAGG GGATGGCTGT AACAGTTCTG GTACCAGAGC TATCGTGCTA GGGGATCCGT   480
```

CGAC                                                                    484

(2) INFORMATION FOR SEQ ID NO:4:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Nicotiana tabacum/Cladosporium fulvum
        (B) STRAIN: Cladosporium fulvum race 2,5

(vii) IMMEDIATE SOURCE:
        (B) CLONE: SP:AVR4

(xi) SEQUENCE DESCRIPTION: SEQ ID NO:4:

```
Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Lys Ala
            20                  25                  30

Pro Lys Thr Gln Pro Tyr Asn Pro Cys Lys Pro Gln Glu Val Ile Asp
        35                  40                  45

Thr Lys Cys Met Gly Pro Lys Asp Cys Leu Tyr Pro Asn Pro Asp Ser
    50                  55                  60

Cys Thr Thr Tyr Ile Gln Cys Val Pro Leu Asp Glu Val Gly Asn Ala
65                  70                  75                  80

Lys Pro Val Val Lys Pro Cys Pro Lys Gly Leu Gln Trp Asn Asp Asn
                85                  90                  95

Val Gly Lys Lys Trp Cys Asp Tyr Pro Asn Leu Ser Thr Cys Pro Val
            100                 105                 110

Lys Thr Pro Gln Pro Lys Pro Lys Lys Gly Gly Val Gly Gly Lys Lys
        115                 120                 125

Ala Ser Val Gly His Pro Gly Tyr
    130                 135
```

(2) INFORMATION FOR SEQ ID NO:5:

(i) SEQUENCE CHARACTERISTICS:
        (A) LENGTH: 484 base pairs
        (B) TYPE: nucleic acid
        (C) STRANDEDNESS: double
        (D) TOPOLOGY: linear (xi) SEQUENCE DESCRIPTION: SEQ ID NO:5:

GTCGACGGAT CCCCTAGCAC GATAGCTCTG GTACCAGAAC TGTTACAGCC ATCCCCTTTC      60

TTGTCCGACT CAATAGCCAG GATGTCCAAC CGACGCCTTC TTCCCTCCGA CACCTCCCTT     120

CTTCGGCTTC GGTTGCGGCG TCTTTACCGG ACACGTACTC AGGTTTGGAT AGTCGCACCA     180

CTTCTTGCCA ACGTTATCGT TCCACTGCAG TCCTTTTGGA CATGGCTTAA CCACAGGCTT     240

CGCATTGCCA ACTTCGTCGA GCGGTACACA CTGTATGTAG GTTGTACAAC TGTCGGGGTT     300

CGGGTAGAGA CAATCCTTGG GACCCATACA CTTGGTGTCG ATGACTTCTT GGGGCTTGCA     360

TGGGTTGTAT GGTTGAGTTT TGGGGGCTTT GGCACGGCAA GAGTGGGATA TTACTAGGAA     420

TAAGAGAAGT GTAGAGACAA GAAGAAATGA AGGCAATTGT GAAAAGAGAA CAAATCCCAT     480

```
CGAT                                                                      484
```

(2) INFORMATION FOR SEQ ID NO:6:

(i) SEQUENCE CHARACTERISTICS:
        (A) LENGTH: 40 amino acids
        (B) TYPE: amino acid
        (D) TOPOLOGY: linear (xi) SEQUENCE DESCRIPTION: SEQ ID NO:6:

```
Lys Asn Met Phe Thr Ile Asn Pro Asn Ala Ser Asp Tyr Cys Tyr Asp
1               5                   10                  15

Ile Arg Thr Tyr Val Asp Ile Gln Ser Tyr Pro Arg Thr Leu Ser Trp
                20                  25                  30

Asn Lys Ser Thr Ser Cys Cys Ser
            35                  40
```

(2) INFORMATION FOR SEQ ID NO:7:

(i) SEQUENCE CHARACTERISTICS:
        (A) LENGTH: 142 amino acids
        (B) TYPE: amino acid
        (D) TOPOLOGY: linear (xi) SEQUENCE DESCRIPTION: SEQ ID NO:7:

```
Phe Ser His Leu Thr Ser Leu His Glu Leu Tyr Met Gly Arg Cys Asn
1               5                   10                  15

Leu Ser Gly Pro Ile Pro Lys Pro Leu Trp Asn Leu Thr Asn Ile Val
                20                  25                  30

Phe Leu His Leu Gly Asp Asn His Leu Glu Gly Pro Ile Ser His Phe
            35                  40                  45

Thr Ile Phe Glu Lys Leu Lys Arg Leu Ser Leu Val Asn Asn Asn Phe
        50                  55                  60

Asp Gly Gly Leu Glu Phe Leu Ser Phe Asn Thr Gln Leu Glu Arg Leu
65                  70                  75                  80

Asp Leu Ser Ser Asn Ser Leu Thr Gly Pro Ile Pro Ser Asn Ile Ser
                85                  90                  95

Gly Leu Gln Asn Leu Glu Cys Leu Tyr Leu Ser Ser Asn His Leu Asn
                100                 105                 110

Gly Ser Ile Pro Ser Trp Ile Phe Ser Leu Pro Ser Leu Val Glu Leu
            115                 120                 125

Asp Leu Ser Asn Asn Thr Phe Ser Gly Lys Ile Gln Glu Phe
        130                 135                 140
```

(2) INFORMATION FOR SEQ ID NO:8:

(i) SEQUENCE CHARACTERISTICS:
        (A) LENGTH: 30 amino acids
        (B) TYPE: amino acid
        (D) TOPOLOGY: linear (xi) SEQUENCE DESCRIPTION: SEQ ID NO:8:

```
Lys Asn Met Phe Thr Val Asn Pro Asn Ala Ser Asp Tyr Cys Tyr Asp
1               5                   10                  15

Arg Arg Thr Leu Ser Trp Asn Lys Ser Thr Ser Cys Cys Ser
                20                  25                  30
```

(2) INFORMATION FOR SEQ ID NO:9:

(i) SEQUENCE CHARACTERISTICS:

```
        (A) LENGTH: 96 amino acids
        (B) TYPE: amino acid
        (D) TOPOLOGY: linear (xi) SEQUENCE DESCRIPTION: SEQ ID NO:9:

Phe Ser His Leu Thr Ser Leu His Lys Leu Tyr Met Ser Arg Ser Asn
1               5                   10                  15

Leu Ser Gly Pro Ile Pro Lys Pro Leu Trp Asn Leu Thr Asn Ile Val
            20              25                  30

Phe Leu Asp Leu Asn Asn Asn His Leu Glu Gly Pro Ile Pro Ser Asn
            35              40              45

Val Ser Gly Leu Arg Asn Leu Gln Ile Leu Trp Leu Ser Ser Asn Asn
        50              55              60

Leu Asn Gly Ser Ile Pro Ser Trp Ile Phe Ser Leu Pro Ser Leu Ile
65                  70                  75                  80

Gly Leu Asp Leu Ser Asn Asn Thr Phe Ser Gly Lys Ile Gln Glu Phe
                85              90                  95
```